(12) United States Patent
Beliaev et al.

(10) Patent No.: US 8,865,913 B2
(45) Date of Patent: Oct. 21, 2014

(54) CRYSTALLINE FORMS AND PROCESSES FOR THEIR PREPARATION

(71) Applicant: BIAL-Portela & C.A., S.A, S. Mamede do Coronado (PT)

(72) Inventors: Alexander Beliaev, S. Mamede do Coronado (PT); David Alexander Learmonth, Alfena (PT); Brian Broadbelt, Buckinghamshire (GB); Ekaterina Albert, West Lafayette, IN (US); Patricia Andres, West Lafayette, IN (US)

(73) Assignee: Bial-Portela & CA, S.A., S. Mamede Do Coronado (PT)

( * ) Notice: Subject to any disclaimer, the term of this patent is extended or adjusted under 35 U.S.C. 154(b) by 0 days.

(21) Appl. No.: 13/922,085

(22) Filed: Jun. 19, 2013

(65) Prior Publication Data

US 2014/0031561 A1     Jan. 30, 2014

Related U.S. Application Data

(63) Continuation of application No. PCT/PT2011/000046, filed on Dec. 21, 2011.

(60) Provisional application No. 61/426,209, filed on Dec. 22, 2010.

(51) Int. Cl.
    *C07D 233/54*     (2006.01)
    *C07D 405/04*     (2006.01)

(52) U.S. Cl.
    CPC .................................. *C07D 405/04* (2013.01)
    USPC ....................................................... 548/311.4

(58) Field of Classification Search
    USPC ........................................................ 548/311.4
    See application file for complete search history.

(56) References Cited

FOREIGN PATENT DOCUMENTS

| WO | 2008136695 A1 | 11/2008 |
| WO | 2012087174 A2 | 6/2012 |
| WO | 2012087174 A3 | 6/2012 |

OTHER PUBLICATIONS

Benedict, Claude R., et al., "Prognostic Significance of Plasma Norepinephrine in Patients with Asymptomatic Left Ventricular Dysfunction," Circulation, Aug. 15, 1996, pp. 690-697, vol. 94, No. 4, American Heart Association, Inc.
Cohn, Jay N., et al., "Plasma Norepinephrine as a Guide to Prognosis in Patients with Chronic Congestive Heart Failure," The New England Journal of Medicine, Sep. 27, 1984, pp. 819-823, vol. 311, No. 13.
Filing receipt and specification for provisional application entitled "Crystalline Forms and Processes for Their Preparation," by Alexander Beliaev, et al., filed Dec. 22, 2010 as U.S. Appl. No. 61/426,209.
Foreign communication from the priority application—International Preliminary Report on Patentability, PCT/PT2011/000046, Jun. 25, 2013, 12 pages.
Foreign communication from the priority application—International Search Report and Written Opinion, PCT/PT2011/000046, Feb. 7, 2013, 15 pages.
Hasking, Gregory J., et al., "Norepinephrine Spillover to Plasma in Patients with Congestive Heart Failure: Evidence of Increased Overall and Cardiorenal Sympathetic Nervous Activity," Circulation, Apr. 1986, pp. 615-621, vol. 73, No. 4, American Heart Association.
Hilfiker, Rolf, et al., "Relevance of Solid-state Properties for Pharmaceutical Products," XP-002525043, 2006, pp. 1-19, Wiley-VCH Verlag GmbH & Co. KGaA, Weinheim.
Leimbach, Jr., Wayne N., et al., "Direct Evidence from Intraneural Recordings for Increased Central Sympathetic Outflow in Patients with Heart Failure," Circulation, 1986, pp. 913-919, vol. 73, No. 5, American Heart Association.
Levine, T. Barry, et al., "Activity of the Sympathetic Nervous System and Renin-Angiotensin System Assessed by Plasma Hormone Levels and Their Relation to Hemodynamic Abnormalities in Congestive Heart Failure," The American Journal of Cardiology, May 1982, pp. 1659-1666, vol. 49.
Parmley, William W., Neuroendocrine Changes in Heart Failure and Their Clinical Relevance, Clin. Cardiol. Aug. 1995, pp. 440-445, vol. 18.
American Psychiatric Association, "Diagnostic and Statistical Manual of Mental Disorders," Fourth Edition, Text Revision, 2000, pp. 429-484 plus 2 cover and publication pages.

*Primary Examiner* — Samantha Shterengarts
(74) *Attorney, Agent, or Firm* — Conley Rose, P.C.; Rodney B. Carroll

(57) ABSTRACT

The present invention relates to crystalline Form A of 1-[(3R)-6,8-difluoro-3,4-dihydro-2H-1-benzopyran-3-yl]-1,3-dihydro-5-[2-[(phenylmethyl)amino]ethyl]-2H-imidazole-2-thione and crystalline Form B of 1-[(3R)-6,8-difluoro-3,4-dihydro-2H-1-benzopyran-3-yl]-1,3-dihydro-5-[2-[(phenylmethyl)amino]ethyl]-2H-imidazole-2-thione, processes for preparing the forms and their uses in medicine. The present invention also relates to the amorphous form of 1-[(3R)-6,8-difluoro-3,4-dihydro-2H-1-benzopyran-3-yl]-1,3-dihydro-5-[2-[(phenylmethyl)amino]ethyl]-2H-imidazole-2-thione processes for preparing it and its uses in medicine.

14 Claims, 18 Drawing Sheets

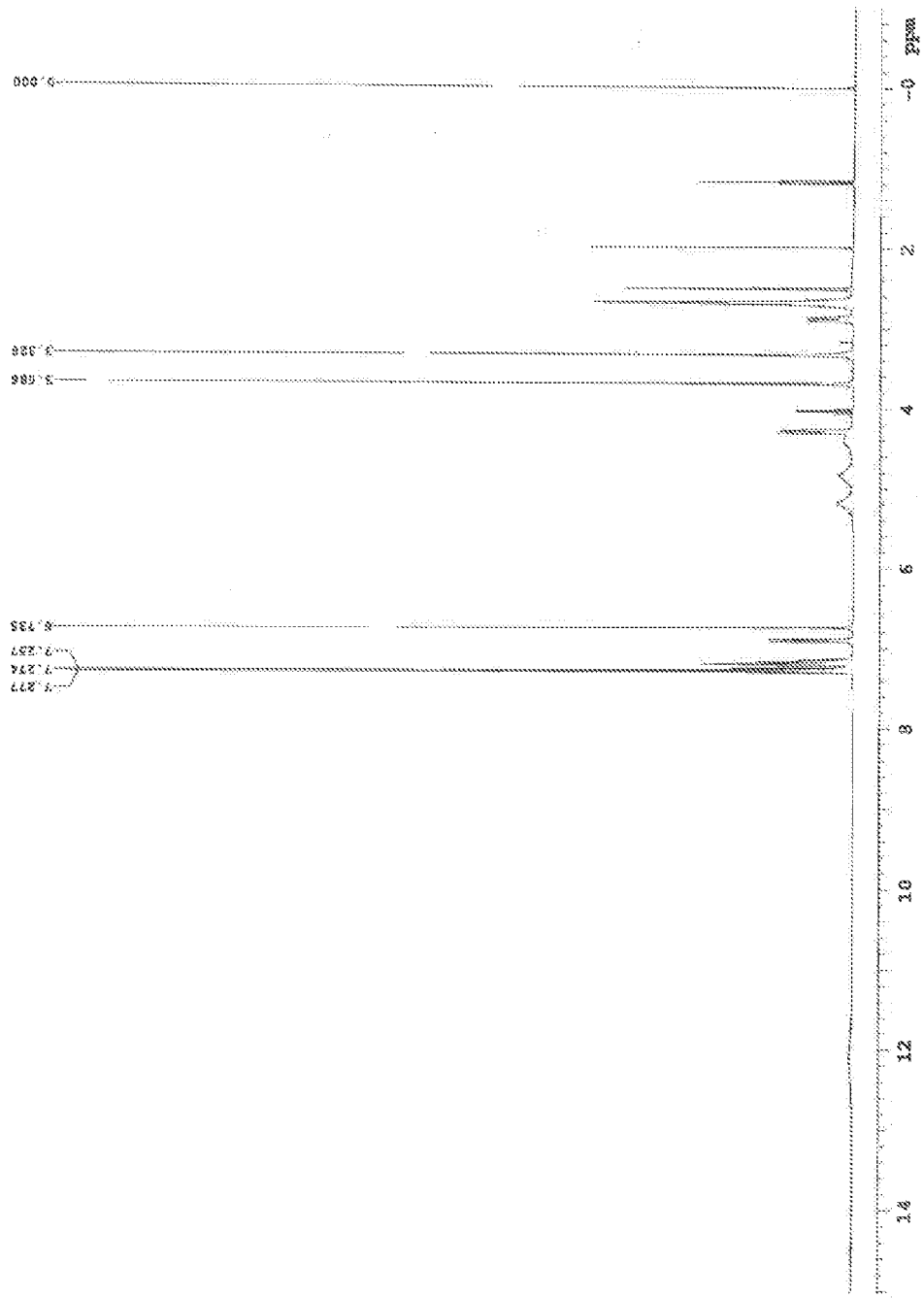

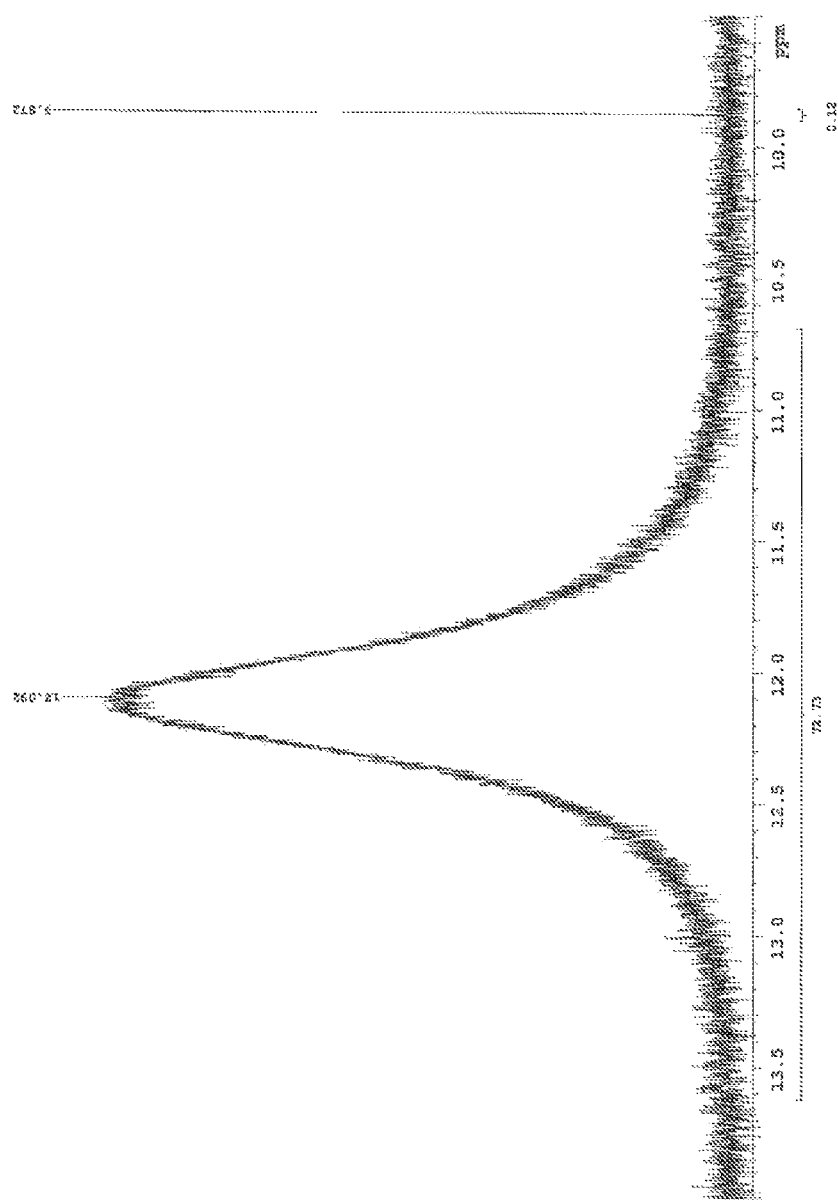

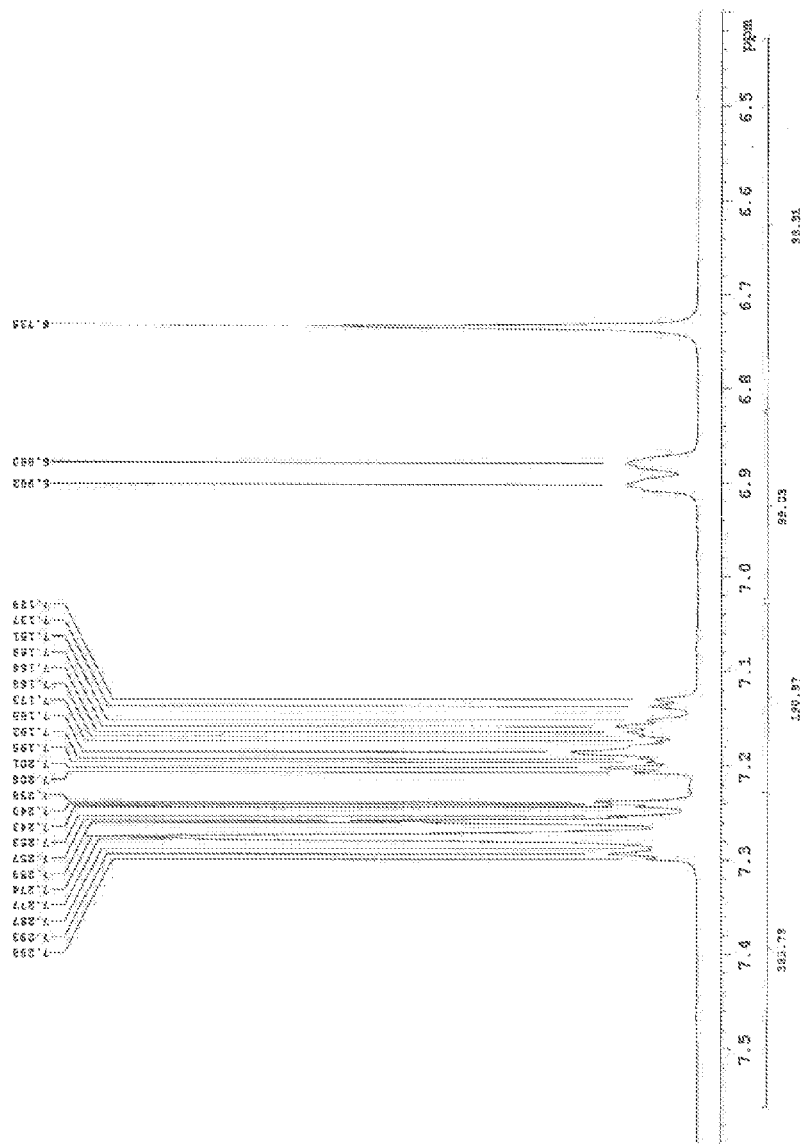

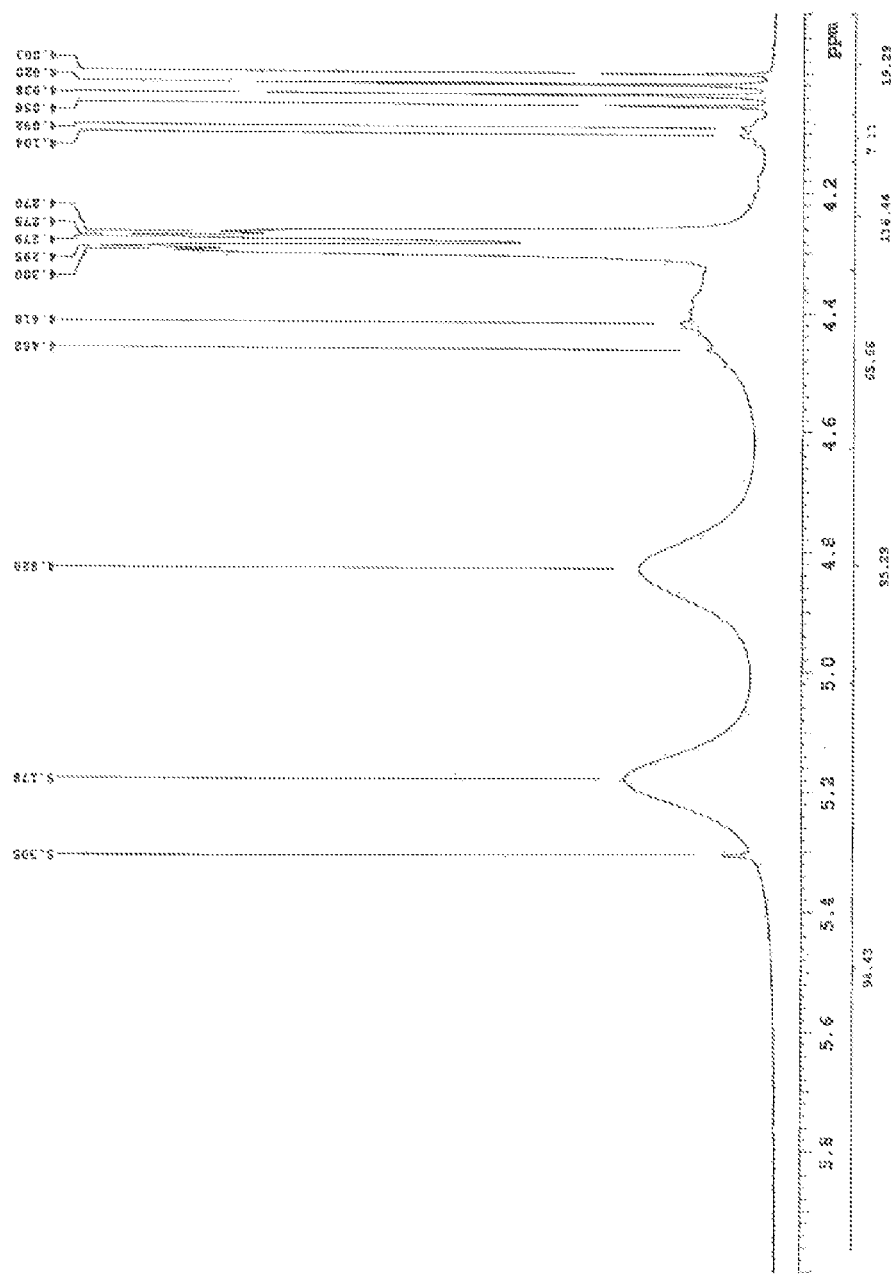

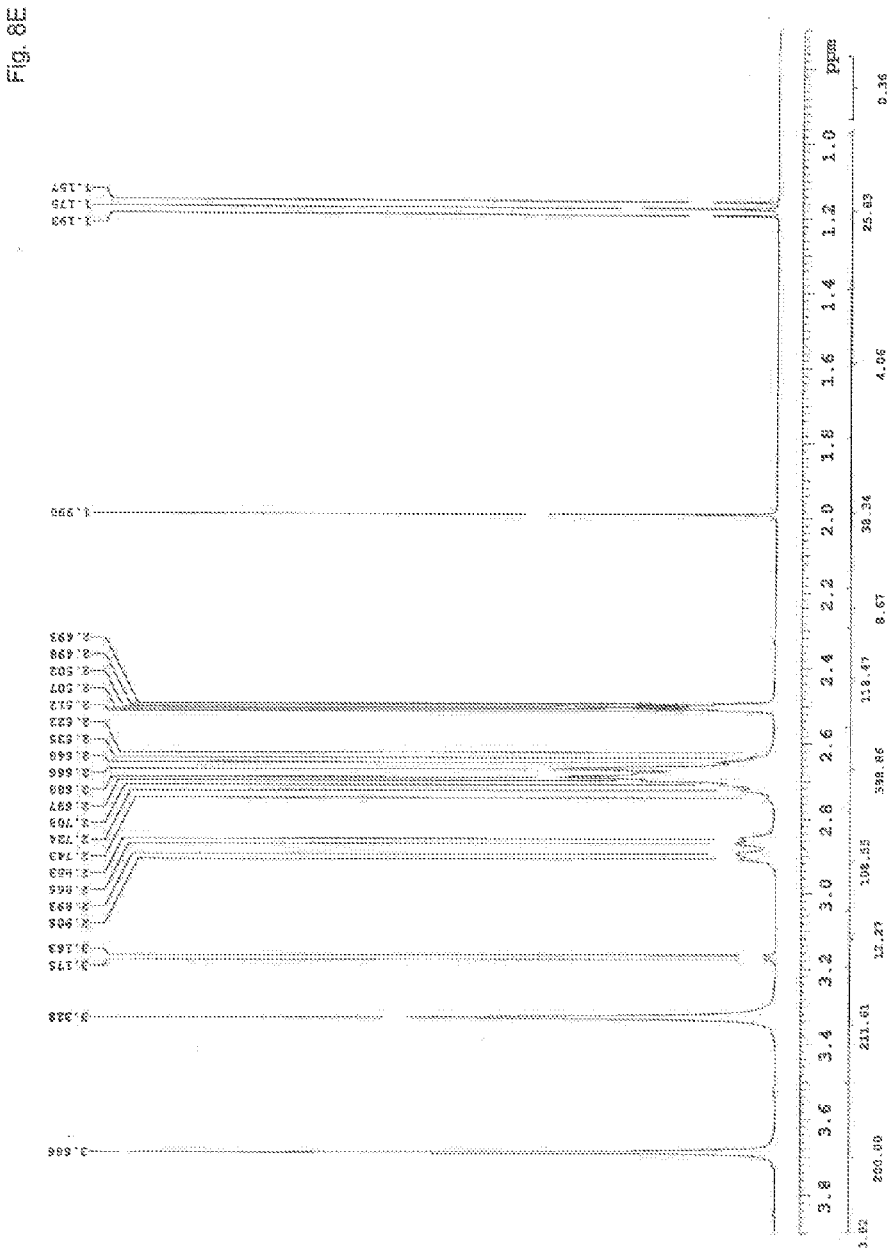

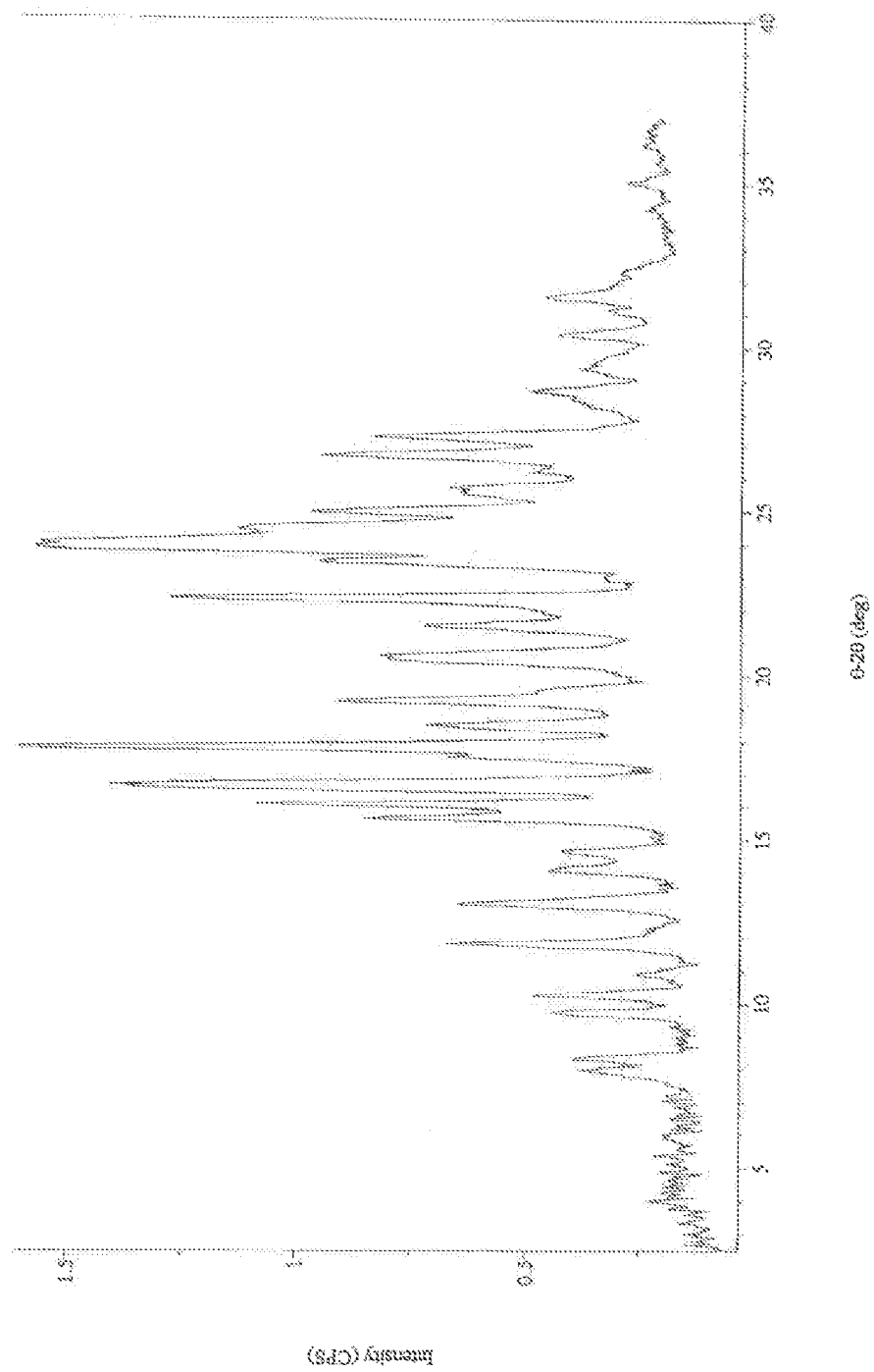

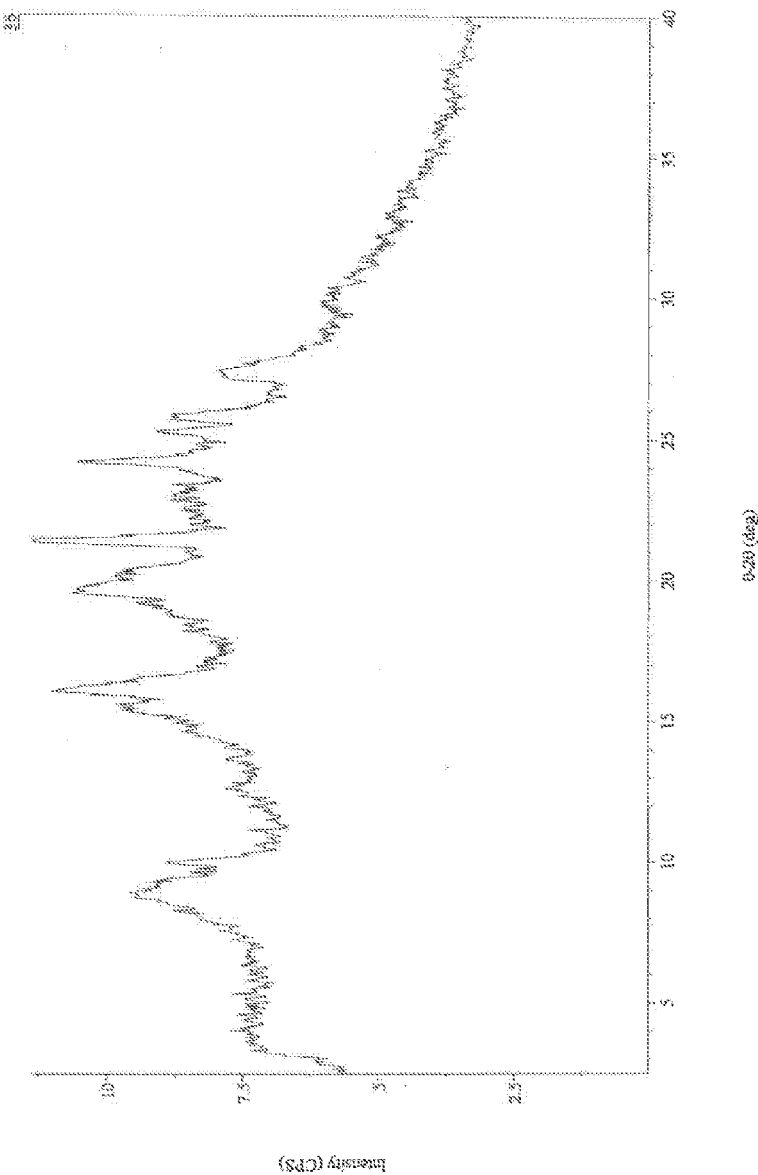

CRYSTALLINE FORMS AND PROCESSES FOR THEIR PREPARATION

CROSS-REFERENCE TO RELATED APPLICATIONS

This application is a continuation of and claims priority to PCT International Application No. PCT/PT2011/000046, filed Dec. 21, 2011 and entitled "Crystalline Forms and Processes for their Preparation," which is a non-provisional application of U.S. Provisional Patent Application No. 61/426,209 filed Dec. 22, 2010, which applications are incorporated herein by reference in their entirety for all purposes.

TECHNICAL FIELD

The present invention relates to novel crystalline forms of 1-[(3R)-6,8-difluoro-3,4-dihydro-2H-1-benzopyran-3-yl]-1,3-dihydro-5-[2-[(phenylmethyl)amino]ethyl]-2H-imidazole-2-thione, i.e. the R enantiomer of

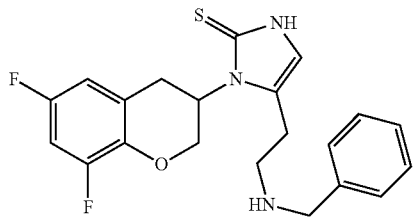 [SMILES: Fc1cc(F)c2c(c1)CC(n1c(CCNCc3ccccc3)c[nH]c1=S)CO2]

and processes for preparing the same.

BACKGROUND AND PRIOR ART

Interest in the development of inhibitors of dopamine-β-hydroxylase (DBH) has centred on the hypothesis that inhibition of this enzyme may provide significant clinical improvements in patients suffering from cardiovascular disorders such as hypertension or chronic heart failure. The rationale for the use of DBH inhibitors is based on their capacity to inhibit the biosynthesis of noradrenaline, which is achieved via enzymatic hydroxylation of dopamine. Activation of neurohumoral systems, chiefly the sympathetic nervous system, is the principal clinical manifestation of congestive heart failure (Parmley, W. W., Clinical Cardiology, 18: 440-445, 1995). Congestive heart failure patients have elevated concentrations of plasma noradrenaline (Levine, T. B. et al., Am. J. Cardiol., 49:1659-1666, 1982), increased central sympathetic outflow (Leimbach, W. N. et al., Circulation, 73: 913-919, 1986) and augmented cardiorenal noradrenaline spillover (Hasking, G. J. et al., Circulation, 73:615-621, 1966). Prolonged and excessive exposure of the myocardium to noradrenaline may lead to down-regulation of cardiac $\beta_1$-adrenoceptors, remodelling of the left ventricle, arrhythmias and necrosis, all of which can diminish the functional integrity of the heart. Congestive heart failure patients who have high plasma concentrations of noradrenaline also have the most unfavourable long-term prognosis (Cohn, J. N. et al., N. Engl. J. Med., 311:819-823, 1984). Of greater significance is the observation that plasma noradrenaline concentrations are already elevated in asymptomatic patients with no overt heart failure and can predict ensuing mortality and morbidity (Benedict, C. R. et al., Circulation, 94:690-697, 1996). An activated sympathetic drive is not therefore merely a clinical marker of congestive heart failure, but may contribute to progressive worsening of the disease.

Potent dopamine-β-hydroxylase inhibitors having high potency and significantly reduced brain access are disclosed in WO 2008/136695. WO 2008/136695 describes compounds of formula I:

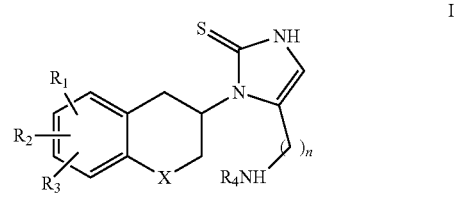

where $R_1$, $R_2$ and $R_3$ are the same or different and signify hydrogens, halogens, alkyl, nitro, amino, alkylcarbonylamino, alkylamino or dialkylamino group; $R_4$ signifies—alkylaryl or—alkylheteroaryl; X signifies $CH_2$, oxygen atom or sulphur atom; n is 2 or 3; including the individual (R)- and (S)-enantiomers or mixtures of enantiomers thereof; and including pharmaceutically acceptable salts and esters thereof, wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyl, alkyloxy, halogen or nitro group; the term halogen means fluorine, chlorine, bromine or iodine; the term heteroaryl means heteroaromatic group. In particular, WO 2008/136695 describes 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione. Processes for the preparation of compounds of formula I, and in particular 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione, are described in WO 2008/136695 and are incorporated by reference herein.

It is known that polymorphic forms of the same drug may have substantially different pharmaceutically important properties such as dissolution characteristics and bioavailability as well as stability of the drug. Furthermore, different forms may have different particle size, hardness and glass transition temperature. Thus, one form may provide significant advantages over other forms of the same drug in solid dosage form manufacture processes, such as accurate measurement of the active ingredients, easier filtration, or improved stability during granulation or storage. Furthermore, a particular process suitable for one form may also provide drug manufacturers several advantages such as economically or environmentally suitable solvents or processes, or higher purity or yield of the desired product.

SUMMARY OF THE INVENTION

The present invention provides crystalline polymorphs of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione and processes for their preparation. The new polymorph forms of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione exhibit high stability upon mechanical and/or aqueous vapor stress. The present invention also provides an amorphous form of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione and processes for its preparation. The amorphous form is also part of the present invention.

Hereinafter, 1-[(3R)-6,8-difluoro-3,4-dihydro-2H-1-benzopyran-3-yl]-1,3-dihydro-5-[2-[(phenylmethyl)amino]ethyl]-2H-imidazole-2-thione shall either be referred to as such or as "compound 2".

In the following description of the present invention, the polymorphic forms are described as having an XRPD pattern with peaks at the positions listed in the respective Tables. It is to be understood that, in one embodiment, the polymorphic form has an XRPD pattern with peaks at the °2θ positions listed ±0.2°2θ with any intensity (% (I/Io)) value; or in another embodiment, an XRPD pattern with peaks at the °2θ positions listed ±0.1°2θ. It is to be noted that the intensity values are included for information only and the definition of each of the peaks is not to be construed as being limited to particular intensity values.

According to one aspect of the present invention, there is provided crystalline Form A of 1-[(3R)-6,8-difluoro-3,4-dihydro-2H-1-benzopyran-3-yl]-1,3-dihydro-5-[2-[(phenylmethyl)amino]ethyl]-2H-imidazole-2-thione.

In an embodiment crystalline Form A of compound 2 is not a solvate, i.e. Form A of compound 2 is in unsolvated form.

According to the present invention, unsolvated means that the thermogravimetric (TGA) curve of crystalline Form A of compound 2 shows a weight loss of less than around 1% wt %, preferably less than around 0.6%, more preferably no weight loss below around 200° C.

According to another aspect of the present invention, there is provided Form A of compound 2 having an XRPD pattern with peaks at 14.0, 16.1, 16.6, 19.2 and 20.4°2θ±0.2°2θ. The XRPD pattern may have further peaks at 15.6 and 18.4°2θ±0.2°2θ.

Form A may be characterised as having an X-ray Powder Diffraction (XRPD) pattern with the peaks presented in Table 1.

TABLE 1

| °2θ | d space (Å) | Intensity (%) |
| --- | --- | --- |
| 14.01 | 6.322 ± 0.045 | 24 |
| 15.58 | 5.688 ± 0.037 | 48 |
| 16.07 | 5.517 ± 0.034 | 100 |
| 16.63 | 5.330 ± 0.032 | 44 |
| 18.40 | 4.821 ± 0.026 | 31 |
| 19.19 | 4.625 ± 0.024 | 64 |
| 20.36 | 4.362 ± 0.021 | 27 |

In an embodiment, Form A is characterised as having an X-ray powder Diffraction (XRPD) pattern with one or more of the peaks presented in Table 2.

TABLE 2

| °2θ | d space (Å) | Intensity (%) |
| --- | --- | --- |
| 7.93 | 11.154 ± 0.142 | 6 |
| 8.01 | 11.038 ± 0.139 | 4 |
| 10.18 | 8.687 ± 0.086 | 1 |
| 11.80 | 7.498 ± 0.064 | 5 |
| 12.26 | 7.222 ± 0.059 | 3 |
| 12.74 | 6.949 ± 0.055 | 6 |
| 14.01 | 6.322 ± 0.045 | 24 |
| 14.54 | 6.090 ± 0.042 | 6 |
| 15.58 | 5.688 ± 0.037 | 48 |
| 16.07 | 5.517 ± 0.034 | 100 |
| 16.48 | 5.378 ± 0.033 | 13 |
| 16.63 | 5.330 ± 0.032 | 44 |
| 17.69 | 5.015 ± 0.028 | 2 |
| 18.40 | 4.821 ± 0.026 | 31 |
| 19.19 | 4.625 ± 0.024 | 64 |
| 19.61 | 4.528 ± 0.023 | 2 |

TABLE 2-continued

| °2θ | d space (Å) | Intensity (%) |
| --- | --- | --- |
| 19.78 | 4.490 ± 0.023 | 2 |
| 20.36 | 4.362 ± 0.021 | 27 |
| 21.05 | 4.221 ± 0.020 | 2 |
| 21.33 | 4.166 ± 0.019 | 11 |
| 21.80 | 4.077 ± 0.019 | 8 |
| 22.05 | 4.032 ± 0.018 | 9 |
| 22.27 | 3.993 ± 0.018 | 15 |
| 23.38 | 3.804 ± 0.016 | 34 |
| 23.75 | 3.746 ± 0.016 | 67 |
| 24.20 | 3.677 ± 0.015 | 71 |
| 24.39 | 3.650 ± 0.015 | 6 |
| 24.92 | 3.573 ± 0.014 | 25 |
| 25.41 | 3.506 ± 0.014 | 13 |
| 25.67 | 3.470 ± 0.013 | 35 |
| 26.63 | 3.348 ± 0.012 | 36 |
| 26.91 | 3.313 ± 0.012 | 6 |
| 27.16 | 3.283 ± 0.012 | 47 |
| 27.43 | 3.252 ± 0.012 | 5 |
| 28.26 | 3.158 ± 0.011 | 19 |
| 28.58 | 3.123 ± 0.011 | 3 |
| 28.77 | 3.104 ± 0.011 | 2 |
| 29.33 | 3.045 ± 0.010 | 7 |

In another embodiment, Form A has the XRPD pattern as shown in FIG. 2.

According to another embodiment of the present invention, there is provided crystalline Form A of 1-[(3R)-6,8-difluoro-3,4-dihydro-2H-1-benzopyran-3-yl]-1,3-dihydro-5-[2-[(phenylmethyl)amino]ethyl]-2H-imidazole-2-thione having a Thermogravimetric Analysis (TGA) thermogram showing a weight loss with an onset temperature of 259° C.±5° C. In an embodiment, the TGA thermogram shows a weight loss with an onset temperature that ranges from around 257° C. to around 262° C. In an embodiment, Form A has a TGA thermogram showing a weight loss with an onset temperature of around 259° C.

In an embodiment, Form A has the TGA thermogram as shown in FIG. 3.

According to another embodiment of the present invention, there is provided crystalline Form A of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione having a Differential Scanning Calorimetry (DSC) thermogram showing an endothermic peak with an onset temperature of 192° C.±2° C. and a peak maximum at 193° C.±2° C. In an embodiment, the DSC thermogram shows an endothermic peak with an onset temperature ranging from around 190° C. to around 192° C. In an embodiment, the DSC shows an endothermic peak with a peak maximum ranging from around 193° C. to around 194° C. In an embodiment, Form A has a DSC thermogram having an endothermic peak with an onset temperature of around 192° C. and a peak maximum at around 193° C. In an embodiment, the DSC thermogram shows a heat of fusion of 141 J/g±10 J/g. In an embodiment, the DSC thermogram shows a heat of fusion ranging from around 139 J/g to around 147 J/g. In an embodiment the DSC thermogram shows a heat of fusion of around 147 J/g.

In an embodiment, Form A of compound 2 has a DSC thermogram as shown in FIG. 4.

In a further embodiment, Form A of compound 2 is a material exhibiting low hygroscopicity over a range of 5% to 95% relative humidity (RH). Material of low hygroscopicity may be defined as a material that exhibits <0.5 wt(weight) % water uptake over a specified relative humidity range.

In a further embodiment, Form A exhibits a negligible loss upon equilibration at ~5% RH. In the context of this specification, "negligible" means less than 0.5 wt %.

In another embodiment, Form A displays around 0.02% wt gain between around 5% to around 75% RH. In an embodiment Form A displays around 0.19 wt % gain between around 75% to around 95% RH. In other embodiment, Form A displays around 0.20 wt % loss between around 95% to around 5% RH with hysteresis between around 85% to around 45% RH upon desorption.

Advantageously, Form A has low hygroscopicity and remains stable as a crystal form upon mechanical and aqueous vapor stress.

In another aspect, the invention provides crystalline Form B of 1-[(3R)-6,8-difluoro-3,4-dihydro-2H-1-benzopyran-3-yl]-1,3-dihydro-5-[2-[(phenylmethyl)amino]ethyl]-2H-imidazole-2-thione.

The crystalline Form B of compound 2 is an ethyl acetate solvate. In an embodiment, Form B comprises between 0.1 and 0.2 moles of ethyl acetate. In an embodiment, Form B comprises around 0.1 moles of ethyl acetate. In another embodiment, form B comprises around 0.2 moles of ethyl acetate.

According to another aspect of the present invention, there is provided Form B of 1-[(3R)-6,8-difluoro-3,4-dihydro-2H-1-benzopyran-3-yl]-1,3-dihydro-5-[2-[(phenylmethyl)amino]ethyl]-2H-imidazole-2-thione, which is an ethyl acetate solvate, preferably comprising between 0.1 and 0.2 moles of ethyl acetate and having an XRPD pattern with peaks at 7.9 to 8.0, 14.0, 16.0 to 16.1, 19.2 and 20.4°2θ±0.2°2θ. The XRPD pattern may have further peaks at 15.6, 16.7 and 18.4°2θ±0.2°2θ.

In another embodiment, Form B of compound 2 is characterised as having an X-ray powder Diffraction (XRPD) pattern with the peaks presented in Table 3.

TABLE 3

| °2θ | d space (Å) | Intensity (%) |
|---|---|---|
| (7.93-7.95) | 11.145 ± 0.142-11.121 ± 0.141 | 16-19 |
| (14.00-14.04) | 6.326 ± 0.045-6.308 ± 0.045 | 20-20 |
| (15.59-15.60) | 5.685 ± 0.036-5.681 ± 0.036 | 58-64 |
| (16.02-16.05) | 5.533 ± 0.035-5.521 ± 0.034 | 100-100 |
| (16.65-16.66) | 5.325 ± 0.032-5.323 ± 0.032 | 81-71 |
| 18.39 | 4.823 ± 0.026 | 48 |
| (19.17-19.20) | 4.630 ± 0.024-4.624 ± 0.024 | 99-92 |
| 20.37 | 4.361 ± 0.021 | 31 |

In an embodiment, Form B is characterised as having an X-ray powder Diffraction (XRPD) pattern with one or more of the peaks presented in Table 4.

TABLE 4

| °2θ | d space (Å) | Intensity (%) |
|---|---|---|
| (7.93-7.95) | 11.145 ± 0.142-11.121 ± 0.141 | 16-19 |
| (11.79-11.85) | 7.504 ± 0.064-7.468 ± 0.063 | 5-6 |
| (12.26-12.30) | 7.219 ± 0.059-7.196 ± 0.059 | 7-8 |
| (12.71-12.75) | 6.964 ± 0.055-6.943 ± 0.055 | 6-7 |
| (14.00-14.04) | 6.326 ± 0.045-6.308 ± 0.045 | 20-20 |
| (14.52-14.53) | 6.101 ± 0.042-6.095 ± 0.042 | 6-6 |
| (15.59-15.60) | 5.685 ± 0.036-5.681 ± 0.036 | 58-64 |
| (16.02-16.05) | 5.533 ± 0.035-5.521 ± 0.034 | 100-100 |
| (16.65-16.66) | 5.325 ± 0.032-5.323 ± 0.032 | 81-71 |
| (17.61-17.69) | 5.036 ± 0.029-5.013 ± 0.028 | 4-3 |
| 18.39 | 4.823 ± 0.026 | 48-58 |
| (19.17-19.20) | 4.630 ± 0.024-4.624 ± 0.024 | 99-92 |
| 20.37 | 4.361 ± 0.021 | 31-34 |
| (21.27-21.30) | 4.177 ± 0.020-4.171 ± 0.019 | 12-10 |
| (21.82-21.84) | 4.073 ± 0.019-4.070 ± 0.018 | 12-19 |
| 22.09 | 4.025 ± 0.018 | 15-21 |
| (22.19-22.24) | 4.005 ± 0.018-3.998 ± 0.018 | 15-20 |
| 23.34 | 3.811 ± 0.016 | 22-26 |

TABLE 4-continued

| °2θ | d space (Å) | Intensity (%) |
|---|---|---|
| (23.72-23.76) | 3.750 ± 0.016-3.745 ± 0.016 | 59-62 |
| (24.18-24.19) | 3.681 ± 0.015-3.679 ± 0.015 | 73-65 |
| (24.83-24.84) | 3.586 ± 0.014-3.584 ± 0.014 | 25-29 |
| 25.38 | 3.510 ± 0.014 | 10-14 |
| (25.61-25.62) | 3.478 ± 0.013-3.477 ± 0.013 | 35-44 |
| 26.65 | 3.345 ± 0.012 | 41 |
| (27.17-27.21) | 3.282 ± 0.012-3.277 ± 0.012 | 49-58 |
| (28.24-28.26) | 3.161 ± 0.011-3.158 ± 0.011 | 16-18 |
| (29.25-29.26) | 3.053 ± 0.010-3.053 ± 0.010 | 8-7 |

As can be seen from Tables 3 and 4, some peak positions are listed as ranges. This is because the material is a variable solvate (in an embodiment, between 0.1 and 0.2 moles of ethyl acetate).

In an embodiment, Form B has the XRPD pattern as shown in FIG. 5.

According to another embodiment of the present invention, there is provided crystalline Form B of compound 2 having a TGA thermogram showing a weight loss with an onset temperature of 257° C.±5° C. and weight loss between around 130° C. and around 200° C. In an embodiment the TGA thermogram further has around 2.3 wt % loss between around 162° C. and around 200° C. or around 4.7 wt % loss between around 138° C. and around 190° C.

In another embodiment, Form B of compound 2 has a TGA thermogram as shown in FIG. 6.

According to another aspect of the present invention, there is provided crystalline Form B of compound 2 having a DSC thermogram showing an endothermic peak with an onset temperature of around 190° C.±2° C. and a peak maximum at around 192° C.±2° C. In an embodiment, the DSC thermogram shows a heat of fusion at around 141 J/g±10 J/g.

In an embodiment, Form B of compound 2 has a DSC thermogram as shown in FIG. 7.

According to another aspect of the present invention, there is provided crystalline Form B of compound 2 having a $^1$H NMR spectrum comprising peaks attributable to ethyl acetate. In an embodiment, the peaks attributable to ethyl acetate are at around 4.0 ppm, around 2.0 ppm and around 1.2 ppm. As will be understood by the skilled person, the $^1$H NMR spectrum will also comprise peaks that are attributable to the protons of 1-[(3R)-6,8-difluoro-3,4-dihydro-2H-1-benzopyran-3-yl]-1,3-dihydro-5-[2-[(phenylmethyl)amino] ethyl]-2H-Imidazole-2-thione.

In an embodiment, crystalline Form B of compound 2 has a $^1$H NMR spectrum as shown in FIG. 8A. In an embodiment, the $^1$H NMR spectrum is as shown in FIGS. 8A to 8E.

According to another aspect of the present invention, there is 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione in amorphous form.

In the context of this specification, "amorphous" means "x-ray amorphous" which means there is an absence of X-ray diffraction peaks in the XRPD pattern of the material. In an embodiment, X-ray amorphous materials are:

nano-crystalline;
crystalline with a very large defect density;
a kinetic amorphous material; or
a thermodynamic amorphous material;
or a combination of the above.

In an embodiment, the amorphous form has an XRPD pattern exhibiting a halo.

In an embodiment, the amorphous form has an XRPD pattern as shown in FIG. 9.

According to another aspect of the present invention, there is provided amorphous 1-[(3R)-6,8-difluoro-3,4-dihydro-2H-1-benzopyran-3-yl]-1,3-dihydro-5-[2-[(phenylmethyl) amino]ethyl]-2H-imidazole-2-thione having a Thermogravimetric Analysis (TGA) thermogram showing a weight loss with an onset temperature of 258° C.±5° C., and around 1.2 wt % loss between around 26° C. and around 71° C.

In an embodiment, the amorphous form has a TGA thermogram as shown in FIG. 10.

In an embodiment, the amorphous 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione has a Cycling Differential Scanning Calorimetry (Cycling DSC) thermogram showing a step change due to the glass transition. In an embodiment, the step change is at a temperature of 50° C.±2° C. In an embodiment, the cycling involves 2 cycles and the glass transition is exhibited in cycle 2.

In an embodiment, the amorphous 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione has a Cycling Differential Scanning Calorimetry (Cycling DSC) thermogram showing an exothermic peak with peak maximum between around 115° C. and around 124° C. In an embodiment, the cycling involves 2 cycles and the exothermic peak is exhibited in cycle 2. In an embodiment, the crystallisation process produces Form A.

In an embodiment, the amorphous form has a cycling DSC thermogram as shown in FIGS. 11 and 12 (cycles 1 and 2, respectively).

In a further embodiment, amorphous compound 2 is a material exhibiting significant hygroscopicity between around 5% and around 75% RH. Material of significant hygroscopicity may be defined as a material that exhibits ≥2.0 wt % water uptake over a specified RH range.

In another embodiment, amorphous compound 2 exhibits around 0.08 wt % gain upon equilibration at around 5% RH.

In an embodiment, amorphous compound 2 displays around 1.2 wt % gain between around 5% and around 75% RH. In an embodiment amorphous compound 2 displays around 8.7 wt % gain between around 75% and around 95% RH. In an embodiment, amorphous compound 2 displays around 8.6 wt % loss between around 95% and around 5% RH and hysteresis over a range of more than 50% RH. The hysteresis may be between around 85% and around 15% RH upon desorption.

The amorphous form is advantageous in that it is a versatile intermediate for use in preparing other forms of compound 2. For example, amorphous compound 2 may be used to prepare Form B of compound 2 when ethyl acetate is used as a solvent in the crystallization process, and amorphous compound 2 may be used to prepare Form A of compound 2 when solvents other than ethyl acetate are used in the crystallization process. Amorphous forms are also useful materials, given the low water solubility of the crystalline forms of compound 2. When being solvated, the amorphous forms do not require the energy to disrupt the crystal lattice that their crystalline counterparts do, thus being better suited to prepare pharmaceutical compositions displaying higher solubility and higher bioavailability.

Crystalline Forms A and B and the amorphous form have been described above in relation to XRPD data, DSC data, TGA data and/or $^1$H NMR data (and solvate mol % data in the case of Form B). It will be understood that the forms may be characterised by each of the sets of data individually or by a combination of one or more of the sets of data.

It will be appreciated that peak positions may vary to a small extent depending on which apparatus is used to analyse a sample. Therefore, all definitions of the polymorphs which refer to peak positions at °2θ values are understood to be subject to variation of ±0.2°2θ. Unless otherwise stated (for example in the Tables with ±values), the °2θ values of the peak positions are ±0.2°2θ.

Advantageously, crystalline Form A as described herein, crystalline Form B as described herein and/or amorphous form as described herein of compound 2 may show additional improved properties, such as, improved bioavailability, solubility, hygroscopicity, dissolution rate, safety profile, stability (heat, air, pressure, light), compatibility with excipients in pharmaceutical formulation, (higher) melting point, density, hardness, longer DβH inhibition, increased DβH inhibition and/or higher peripheral selectivity when used in a medicament over other forms of compound 2. Also advantageously, crystalline Form A as described herein, crystalline Form B as described herein and/or amorphous form as described herein of compound 2 may show additional improved properties, such as, storage stability, filterability during process (crystal size, particle size distribution), processability (e.g. not sticking to equipment), easy drying, purity and yield and/or wettability, in terms of the manufacturing process over other forms of compound 2.

According to another aspect of the present invention, there is provided a process to purify crystalline Form A of compound 2 which comprises the recrystallization of (R)-5-(2-(benzylamino)ethyl)-1-(6,8-difluorochroman-3-yl)-1H-imidazole-2(3H)-thione hydrochloride in at least one organic solvent. Preferably the organic solvent is a mixture of toluene and methanol. In a preferred embodiment toluene and methanol are present in the mixture in a proportion of 62:38 w/w. In an embodiment the organic solvent is distilled off and replaced with toluene.

Suitably, the purification process further comprises the conversion of (R)-5-(2-(benzylamino)ethyl)-1-(6,8-difluorochroman-3-yl)-1H-imidazole-2(3H)-thione hydrochloride to (R)-5-(2-(benzylamino)ethyl)-1-(6,8-difluorochroman-3-yl)-1H-imidazole-2(3H)-thione. In an embodiment the conversion of (R)-5-(2-(benzylamino)ethyl)-1-(6,8-difluorochroman-3-yl)-1H-imidazole-2(3H)-thione hydrochloride is achieved using an alkali metal hydroxide. Preferably, the alkali metal hydroxide is sodium hydroxide. In an embodiment the conversion is carried out in a mixture of methanol and water.

Advantageously, the purity of (R)-5-(2-(benzylamino) ethyl)-1-(6,8-difluorochroman-3-yl)-1H-imidazole-2(3H)-thione prepared by the purification process of the present invention is at least 95%, preferably at least 98%, most preferably ≥99.0%.

According to another aspect of the present invention, there is provided the use of Form A as described herein, Form B as described herein, or amorphous form as described herein of 1-[(3R)-6,8-difluoro-3,4-dihydro-2H-1-benzopyran-3-yl]-1, 3-dihydro-5-[2-[(phenylmethyl)amino]ethyl]-2H-Imidazole-2-thione and one or more pharmaceutically acceptable carriers or excipients.

The pharmaceutical formulation may also include at least one other active pharmaceutical ingredient.

In another aspect, the invention also provides methods of treating disorders where a reduction in the hydroxylation of dopamine to noradrenaline is of therapeutic benefit, which comprises administering a mammal in need thereof an effective amount of Form A as described herein, Form B as described herein, or the amorphous form as described herein of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione.

According to another aspect of the present invention, there is provided the use of Form A as described herein, Form B as described herein, or the amorphous form as described herein of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione in the manufacture of a medicament for treatment of anxiety disorders, migraines, cardiovascular disorders, hypertension, chronic or congestive heart failure, angina, arrhythmias, and circulatory disorders such as Raynaud's phenomenon.

In the above methods Form A as described herein, Form B as described herein, or the amorphous form as described herein of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione for use in the treatment of anxiety disorders, migraines, cardiovascular disorders, hypertension, chronic or congestive heart failure, angina, arrhythmias, and circulatory disorders such as Raynaud's phenomenon.

According to another aspect of the present invention, there is provided the use of Form A as described herein, Form B as described herein, or the amorphous form as described herein of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione in the manufacture of a medicament for inhibition of DβH.

According to another aspect of the present invention, there is provided Form A as described herein, Form B as described herein, or the amorphous form as described herein of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione for use in the inhibition of DβH.

In the above aspects, Form A as described herein, Form B as described herein, or the amorphous form as described herein of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione may be used in combination with at least one other active pharmaceutical ingredient.

In another aspect, the invention also provides methods of treating disorders where a reduction in the hydroxylation of dopamine to noradrenaline is of therapeutic benefit, which comprises administering a mammal in need thereof an effective amount of Form A as described herein, Form B as described herein, or the amorphous form as described herein of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione.

In another aspect, the invention also provides methods of treating one or more of the following indications: anxiety disorders, migraines, cardiovascular disorders, hypertension, chronic or congestive heart failure, angina, arrhythmias, and circulatory disorders such as Raynaud's phenomenon, which comprises administering a mammal in need thereof an effective amount of Form A as described herein, Form B as described herein, or the amorphous form as described herein of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione.

In the above methods Form A as described herein, Form B as described herein, or the amorphous form as described herein of 1-[(3R)-6,8-difluoro-3,4-dihydro-2H-1-benzopyran-3-yl]-1,3-dihydro-5-[2-[(phenylmethyl)amino]ethyl]-2H-Imidazole-2-thione may be administered in combination with at least one other active pharmaceutical ingredient.

The combination treatment or use described herein may involve the simultaneous or staggered administration.

Anxiety disorders include but are not restricted to generalized anxiety disorders, social anxiety disorders, post-traumatic stress disorder, acute distress disorder, obsessive compulsive disorders, panic disorders such as panic attacks, and phobias such as agoraphobia, social phobias, specific phobias. Further anxiety disorders treatable using compounds of the present invention may be found in on pages 429-484 of American Psychiatric Association: Diagnostic and Statistic Manual of Mental Disorders, 4$^{th}$ edition, Text Revision, Washington, D.C., American Psychiatric Association, 2000.

As used herein, the term 'treatment' and variations such as 'treat' or 'treating' refer to any regime that can benefit a human or non-human animal. The treatment may be in respect of an existing condition or may be prophylactic (preventative treatment). Treatment may include curative, alleviation or prophylactic effects.

BRIEF DESCRIPTION OF THE FIGURES

Reference is made to the accompanying Figures in which:
FIG. 8A shows the $^1$H NMR spectrum for Form B of compound 2
PARAMETERS:
in DMSO-d6 w/TMS referenced to TMS at 0.0 ppm
Probe: 5 mm_VIDP
Solvent: DMSO
Ambient temperature
Spin rate: 20 Hz
Pulse sequence: s2pul
Relax. delay: 5.000 sec
Pulse width: 8.0 usec (90.0 deg.)
Acq. time: 2.500 sec
Spectral width: 6400.0 Hz (16.008 ppm)
40 scans
Acquired points: 32000
Observe nucleus: H1 (399.7957232 MHz)
DATA PROCESSING:
Line broadening: 0.2 Hz
FT size 131072
Index of peaks in FIG. 8A:

Figure 1:
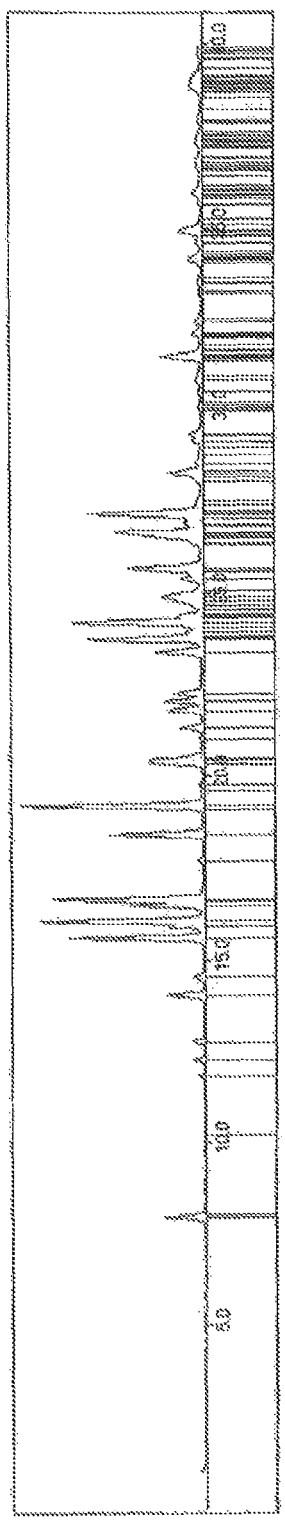
FIG. 1 shows the Tentative Indexing Solution for compound 2—bars indicate allowed reflections based on the unit cell dimensions and the assigned space group (P1, #1)

| INDEX | FREQUENCY | PPM | HEIGHT |
|---|---|---|---|
| 1 | 2909.375 | 7.277 | 113.2 |
| 2 | 2908.203 | 7.274 | 137.0 |
| 3 | 2901.465 | 7.257 | 78.0 |
| 4 | 2692.480 | 6.735 | 87.1 |
| 5 | 1473.730 | 3.686 | 141.8 |
| 6 | 1330.664 | 3.328 | 80.8 |
| 7 | −0.000 | −0.000 | 64.0 |

FIG. 8B shows an enlarged section of the $^1$H NMR spectrum for Form B of compound 2 (as shown in FIG. 8A)
Parameters: as for FIG. 8A
Index of peaks in FIG. 8B:

| INDEX | FREQUENCY | PPM | HEIGHT |
|---|---|---|---|
| 1 | 4034.277 | 12.092 | 132.0 |
| 2 | 3946.875 | 9.872 | 80.4 |

FIG. 8C shows an enlarged section of the $^1$H NMR spectrum for Form B of compound 2 (as shown in FIG. 8A)
Parameters: as for FIG. 8A
Index of peaks in FIG. 8C:

| INDEX | FREQUENCY | PPM | HEIGHT |
|---|---|---|---|
| 1 | 2917.871 | 7.290 | 11.5 |
| 2 | 2915.723 | 7.293 | 19.4 |
| 3 | 2913.477 | 7.287 | 10.9 |
| 4 | 2909.375 | 7.277 | 109.1 |
| 5 | 2908.203 | 7.274 | 132.0 |
| 6 | 2902.246 | 7.259 | 59.4 |
| 7 | 2901.465 | 7.257 | 75.2 |
| 8 | 2899.609 | 7.253 | 19.6 |
| 9 | 2895.605 | 7.243 | 13.4 |
| 10 | 2894.434 | 7.240 | 19.3 |
| 11 | 2893.652 | 7.238 | 22.4 |
| 12 | 2881.055 | 7.206 | 14.1 |
| 13 | 2879.004 | 7.201 | 21.0 |
| 14 | 2876.660 | 7.195 | 11.1 |
| 15 | 2875.293 | 7.192 | 13.1 |
| 16 | 2872.461 | 7.185 | 27.7 |
| 17 | 2867.773 | 7.173 | 9.2 |
| 18 | 2865.820 | 7.168 | 13.0 |
| 19 | 2863.965 | 7.164 | 15.2 |
| 20 | 2861.719 | 7.158 | 17.9 |
| 21 | 2859.002 | 7.151 | 11.2 |
| 22 | 2853.223 | 7.137 | 10.0 |
| 23 | 2850.195 | 7.129 | 9.3 |
| 24 | 2759.473 | 6.902 | 15.4 |
| 25 | 2750.408 | 6.800 | 15.5 |
| 26 | 2692.480 | 6.735 | 84.0 |

FIG. 8D shows an enlarged section of the $^1$H NMR spectrum for Form B of compound 2 (as shown in FIG. 8A)
Parameters: as for FIG. 8A
Index of peaks in FIG. 8D:

| INDEX | FREQUENCY | PPM | HEIGHT |
|---|---|---|---|
| 1 | 2120.996 | 5.305 | 10.5 |
| 2 | 2070.215 | 5.178 | 29.7 |
| 3 | 1930.176 | 4.828 | 26.8 |
| 4 | 1783.984 | 4.462 | 13.7 |
| 5 | 1766.211 | 4.418 | 18.9 |
| 6 | 1719.141 | 4.300 | 117.4 |
| 7 | 1716.992 | 4.295 | 132.0 |
| 8 | 1710.645 | 4.279 | 116.1 |
| 9 | 1709.180 | 4.275 | 126.0 |
| 10 | 1706.934 | 4.270 | 108.8 |
| 11 | 1640.918 | 4.104 | 7.7 |
| 12 | 1636.035 | 4.092 | 7.3 |
| 13 | 1621.582 | 4.056 | 33.8 |
| 14 | 1614.453 | 4.038 | 100.1 |
| 15 | 1607.324 | 4.020 | 101.4 |
| 16 | 1600.195 | 4.003 | 35.0 |

FIG. 8E shows an enlarged section of the $^1$H NMR spectrum for Form B of compound 2 (as shown in FIG. 8A)
Parameters: as for FIG. 8A
Index of peaks in FIG. 8E:

| INDEX | FREQUENCY | PPM | HEIGHT |
|---|---|---|---|
| 1 | 1473.730 | 3.686 | 132.0 |
| 2 | 1330.664 | 3.328 | 75.2 |
| 3 | 1269.434 | 3.175 | 2.4 |
| 4 | 1264.648 | 3.163 | 2.7 |
| 5 | 1161.914 | 2.906 | 7.6 |
| 6 | 1156.738 | 2.893 | 8.6 |
| 7 | 1145.703 | 2.866 | 8.4 |
| 8 | 1140.527 | 2.853 | 7.4 |
| 9 | 1096.582 | 2.743 | 2.0 |
| 10 | 1080.965 | 2.724 | 7.2 |
| 11 | 1082.812 | 2.708 | 11.6 |
| 12 | 1078.125 | 2.697 | 27.7 |
| 13 | 1074.609 | 2.688 | 44.4 |
| 14 | 1065.918 | 2.666 | 46.1 |
| 15 | 1058.594 | 2.648 | 12.9 |
| 16 | 1053.516 | 2.635 | 6.0 |
| 17 | 1048.145 | 2.622 | 2.0 |
| 18 | 1004.102 | 2.512 | 14.2 |
| 19 | 1002.246 | 2.507 | 29.9 |
| 20 | 1000.391 | 2.502 | 40.8 |
| 21 | 998.535 | 2.490 | 28.9 |
| 22 | 996.777 | 2.493 | 13.3 |
| 23 | 795.410 | 1.990 | 46.7 |

-continued

| INDEX | FREQUENCY | PPM | HEIGHT |
|---|---|---|---|
| 24 | 476.855 | 1.193 | 13.5 |
| 25 | 469.727 | 1.175 | 27.5 |
| 26 | 462.598 | 1.157 | 13.3 |

Figure 9:
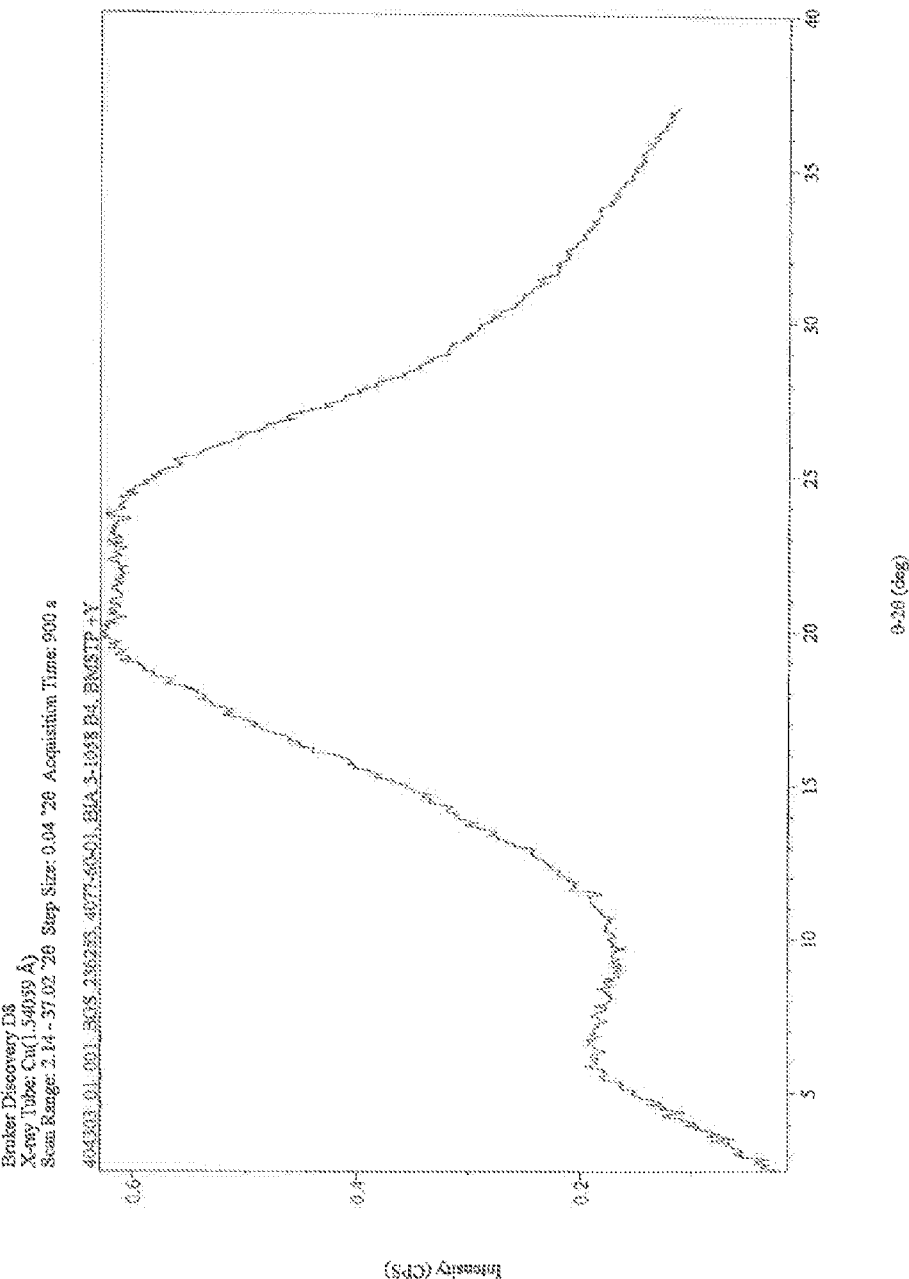

FIG. 9 shows the XRPD of compound 2 in amorphous form

Figure 10:
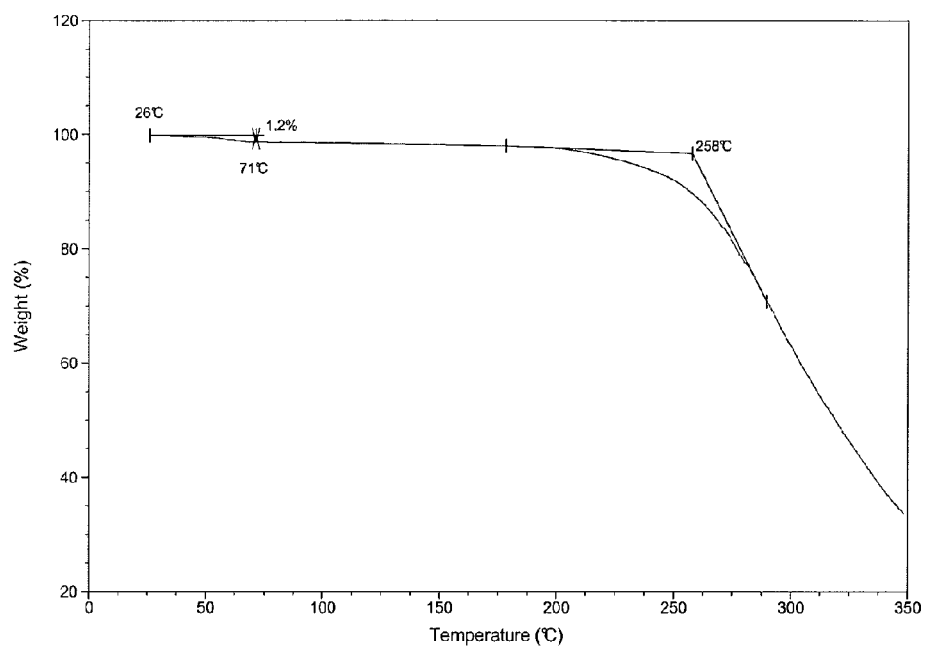
Figure 11:
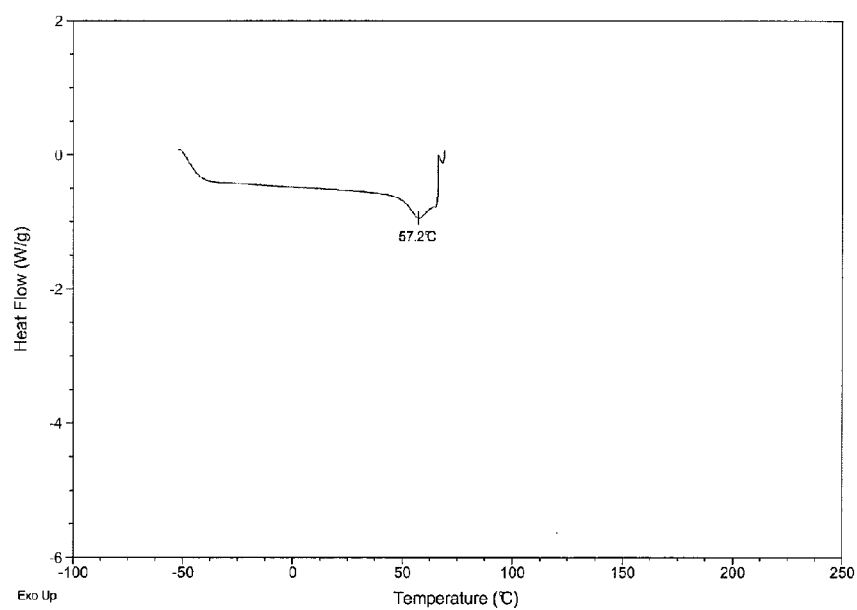
Figure 12:
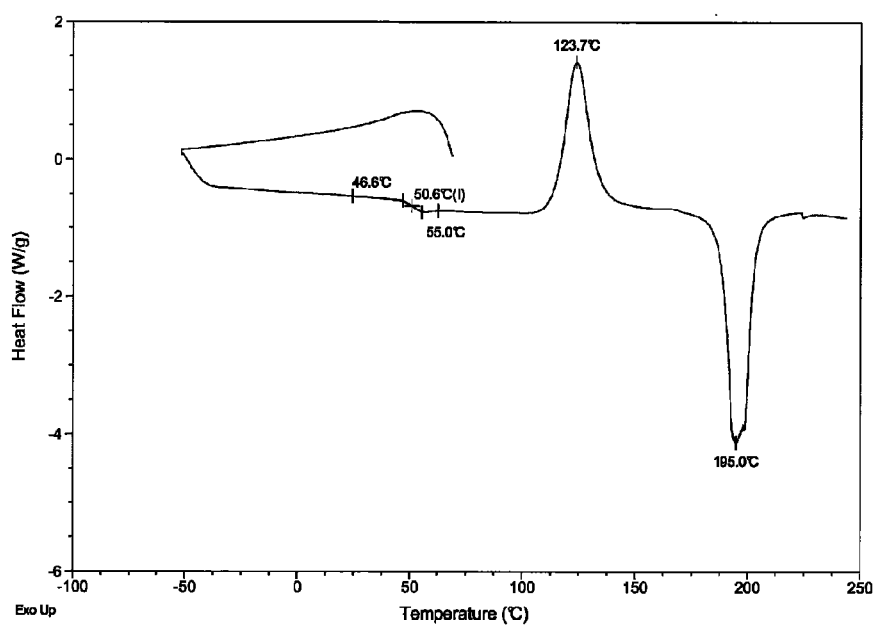

FIG. 10 shows the TGA thermogram of compound 2 in amorphous form
Method: 00-350-10
Instrument: TGA Q5000 V3.3 Build 250
Universal V4.4A TA Instruments FIG. 11 shows Cycling Differential Scanning Calorimetry Analysis of compound
2 in amorphous form—cycle 1
Method: (−50)-(70-(−50)-250)-20
Instrument: 2920 MDSC V2.6A
Universal V4.4A TA Instruments FIG. 12 shows Cycling Differential Scanning Calorimetry Analysis of compound 2 in amorphous form—cycle 2
Method: (−50)-(70-(−50)-250)-20
Instrument: 2920 MDSC V2.6A
Universal V4.4A TA Instruments FIG. 13 shows the XRPD pattern of Material C of compound 2
PARAMETERS:
Bruker Discovery D8
X-ray tube: Cu(1.54059 Å)
Scan range: 2.12-37.00°2θ
Step size: 0.02°2θ
Acquisiting time: 900 s
Image by File Monkey v3.2.3

FIG. 14 shows the XRPD pattern of Material D of compound 2
PARAMETERS:
INEL XRG-3000
X-ray tube: 1.54187000 Å
Voltage: 40 kV
Amperage: 30 mA
Step size: approximately 0.03°2θ
Acquisition time: 300 s
Spinning capillary
Image by File Monkey v3.2.3

DETAILED DESCRIPTION

The analysis of the present invention has shown Form A to be an unsolvated material of low hygroscopicity melting at ~187.9-192.2° C., and Form B to be a non-stoichiometric ethyl acetate solvate. The data for both forms was consistent with materials composed primarily of a single crystalline phase. Form A was characterised using X-ray Powder Diffraction (XRPD), Thermogravimetric Analysis (TGA) and Differential Scanning Calorimetry (DSC). Form B was characterised using XRPD, TGA, DSC and $^1$H NMR spectroscopy.

Form A remained stable as a crystal form upon mechanical and aqueous vapor stress.

To facilitate a better understanding of the present invention, the following examples of certain aspects of some embodiments are given. In no way should the following examples be read to limit, or define, the scope of the invention.

EXPERIMENTAL

Experimental Methods

Preparation of Compound 2
Six lots of compound 2 (designated as lots 1, 2, 3, 4, 5 and 6) were prepared. The starting materials were prepared according to the following experimental protocols.
Lot 1 (Form A)
To a suspension of (R)-5-(2-aminoethyl)-1-(6,8-difluorochroman-3-yl)-1H-imidazole-2(3H)-thione (6.23 g, 20 mmol) in a mixture of Dichloromethane (DCM-40 ml) and Methanol (40.0 ml) was added BENZALDEHYDE (2.230 ml, 22.00 mmol). To the resulting clear solution SODIUM CYANOBOROHYDRIDE (1.9 g, 28.7 mmol) was added in portions at 20-25° C. to avoid intensive foaming and the solution was stirred at 20-25° C. for 40 h. The solution was quenched at 20-25° C. with 1N HCl (35 ml), neutralised with 3N NaOH (35 ml), the mixture was extracted with DCM (200 ml). The organic phase was washed with brine, dried (MgSO4), evaporated to dryness. The oily residue crystallised from 2-propanol (40 ml) at 20-25° C. over a week-end. The crystals were collected, washed with 2-propanol, dried to give 5.2 g of the crude product. Re-crystallisation from 2-propanol-DCM hasn't removed all impurities. Everything collected, evaporated with silica, applied on a column, eluted with Ethyl Acetate (EA)->EA-MeOH 9:1->4:1, fractions 8-25 collected to give 3.8 g. Re-crystallised from 2-propanol (45 ml) and DCM (120 ml, removed on a rotavap) to give 2.77 g=>initial lot (a) (HPLC 98.3% area) and 0.3 g of undissolved filtered off, by TLC right product. Initial lot (a) re-crystallised from 2-propanol (35 ml) and DCM (95 ml, removed on a rotavap) to give 2.51 g=>initial lot (b) (HPLC 98.3% area). Combined with the above undissolved, re-crystallised from acetonitrile (200 ml, reflux to ice bath) to give 2.57 g=>initial lot (c) (HPLC 98.8% area). Re-crystallised from acetonitrile (180 ml, reflux to 15° C.) to give 2.25 g=>Lot 1 (HPLC 99.2% area), mp 190-92° C.
Lot 2 (Form A)
(R)-5-(2-(benzylamino)ethyl)-1-(6,8-difluorochroman-3-yl)-1H-imidazole-2(3H)-thione (12 g, 29.9 mmol) was dissolved with heating to reflux in Tetrahydrofuran (300 ml), the solution was cooled to 5-10° C., Water (510 ml) was added slowly (approx 10 min) with stirring. The mixture was stirred for 1 h, solid was collected, washed with water, dried to give 11.73 g of product, by HPLC 1% of (R)-5-(2-Aminoethyl)-1-(6,8-difluorochroman-3-yl)-1,3-dihydroimidazole-2-thione hydrochloride and 1% of less polar impurity. The product was dissolved in Tetrahydrofuran (300 ml) with heating to reflux, 2-Propanol (150 ml) was added, the solution was concentrated to approx 100 ml (crystallisation occurred), stirred in ice for 1.5 h. Solid was collected, washed with 2-propanol, dried to give 11.2 g of product, by HPLC 0.8% of (R)-5-(2-aminoethyl)-1-(6,8-difluorochroman-3-yl)-1H-imidazole-2(3H)-thione hydrochloride and 0.5% of less polar impurity. The product was dissolved in Tetrahydrofuran (300 ml) with heating to reflux, 2-Propanol (150 ml) was added, the solution was concentrated to approx 100 ml (crystallisation occurred), stirred at 20-25° C. for 1 h. Solid was collected, washed with 2-propanol, dried to give (R)-5-(2-(benzylamino)ethyl)-1-(6,8-difluorochroman-3-yl)-1H-imidazole-2(3H)-thione (10.22 g, 25.5 mmol, 85% yield).,
Lot 3 (form B)
To (R)-5-(2-aminoethyl)-1-(6,8-difluorochroman-3-yl)-1H-imidazole-2(3H)-thione (2.36 g, 7.58 mmol) in a mixture of Methanol (15.00 ml) and Dichloromethane (15 ml) was added BENZALDEHYDE (0.845 ml, 8.34 mmol). To the resulting clear solution SODIUM CYANOBOROHYDRIDE (0.702 g, 10.61 mmol) was added in portions at 20-25° C. to avoid intensive foaming and the solution was stirred at 20-25° C. for 40 h. The solution was quenched at 20-25° C. with 1N HCl (12 ml), neutralised with 3N NaOH (12 ml), the mixture was extracted with DCM (100 ml). The organic phase was washed with brine, dried (MgSO$_4$), evaporated to dryness. The residue was purified on a column with EA-MeOH 9:1 as eluent, fractions collected, concentrated to approx 20 ml, cooled in ice. The precipitate collected, washed with Ethyl Acetate-Petroleum Ether 1:1, dried on air to give (R)-5-(2-(benzylamino)ethyl)-1-(6,8-difluorochroman-3-yl)-1H-imidazole-2(3H)-thione (1.55 g, 3.86 mmol, 50.9% yield).

Lot 4 (Form A)

To a 500 mL flask set up for atmospheric distillation was added (R)-5-(2-(benzylamino)ethyl)-1-(6,8-difluorochroman-3-yl)-1H-imidazole-2(3H)-thione (20 g, 49.8 mmol) and Tetrahydrofuran (400 ml) to afford a suspension. The suspension was heated until full dissolution was achieved (61° C.) whereupon it was filtered. The resulting solution was then heated to 66° C. in order to commence the distillation. A mixture of Water (125 ml) & 2-Propanol (125 ml) was added at the same rate as the distillate was collected. The distillation was continued until 400 mL of distillate was collected. Crystallisation commenced after ~320 mL of distillate was collected. The suspension was cooled to 20° C. and aged for 45 min. before filtering and washing with additional 2-propanol (80 mL) and then dried under vacuum at 50° C. overnight to give (R)-5-(2-(benzylamino)ethyl)-1-(6,8-difluorochroman-3-yl)-1H-imidazole-2(3H)-thione (18.79 g, 94%).

Lot 5 (Form A)

To a mixture of Methanol (66 L) and Water (10 L) at 20° C. was added purified (R)-5-(2-(benzylamino)ethyl)-1-(6,8-difluorochroman-3-yl)-1H-imidazole-2(3H)-thione hydrochloride (4.37 kg, 9.98 mol) to afford a suspension. The reaction mixture was then heated to 67° C. to affect complete dissolution, whereupon 1N Sodium hydroxide (10.48 L, 10.48 mol, 1.05 eq) was added in a single portion. The reaction mixture was adjusted back to 67° C. and held at 67° C. for 30 min. The reaction mixture was then cooled to 20° C. and aged at 20° C. for at least 30 min. The reaction was then filtered and the filter cake washed with aqueous Methanol (1:1 v/v, 20 L), sucked down for 15 min. and then dried at 45° C. under vacuum, to afford (R)-5-(2-(benzylamino)ethyl)-1-(6,8-difluorochroman-3-yl)-1H-imidazole-2(3H)-thione (3.855 kg, 96%) as a pale tan crystalline solid.

Lot 6 (Form A)

A 250 L reactor was charged with 10.22 kg of purified (R)-5-(2-(benzylamino)ethyl)-1-(6,8-difluorochroman-3-yl)-1H-imidazole-2(3H)-thione hydrochloride, 113.0 kg of Methanol was added and the reaction mixture was heated to 47.3° C. with stirring at 120 rpm. A resulting clear brown solution was filtered warm through a GAF filter into a 200 L drum and the filter was flushed with 8.0 kg of Methanol. The reactor was cleaned with 45.0 kg of Methanol, the filtered Methanol solution was transferred from the 200 L drum into the 250 L reactor and the solution was heated to 46.3° C. with stirring at 120 rpm. At this temperature 23.5 kg of water was added during 10 min, the solution was heated to 64.3° C. during 60 min (reflux) and 26.1 kg of a solution of 1.2 kg sodium hydroxide in 30.6 kg water was added at 64.5-65.3° C. during 90 min (reflux; exotherm). The resulting beige suspension was stirred at 65.2-66.9° C. during 45 min, cooled 58-60° C. and sampled for pH-control (pH 11). The suspension was cooled to 24.8° C. during 1 h 55 min, stirred at this temperature during 13 h. The suspension was transferred into the centrifuge (filter cloth type: Lanz Anliker PP20) and centrifuged in one portion. The 250 L reactor was charged with 20.0 kg water and 16.0 kg of Methanol and stirred at 23.0° C. during 10 min. The filter cake was washed with the methanol mixture, the wet product (8.84 kg) was transferred to the tray dryer and dried at 52.2° C. and 290-1 mbar during 68 h 44 min to give 8.45 kg of (R)-5-(2-(benzylamino)ethyl)-1-(6,8-difluorochroman-3-yl)-1H-imidazole-2(3H)-thione.

Within the context of the present patent application, purified (R)-5-(2-(benzylamino)ethyl)-1-(6,8-difluorochroman-3-yl)-1H-imidazole-2(3H)-thione hydrochloride means that the compound presents a purity at least 95%, preferably at least 98%, most preferably ≥99.0%.

A. Preparation of purified (R)-5-(2-(benzylamino) ethyl)-1-(6,8-difluorochroman-3-yl)-1H-imidazole-2 (3H)-thione hydrochloride Stage 1: Crude (R)-5-(2-(benzylamino)ethyl)-1-(6,8-difluorochroman-3-yl)-1H-imidazole-2(3H)-thione "Crude Compound 2"

A 250 L reactor was charged with 12.25 kg of (R)-5-(2-aminoethyl)-1-(6,8-difluorochroman-3-yl)-1H-imidazole-2(3H)-thione hydrochloride, 114.82 kg of 2-propanol was added and the mixture was stirred at maximum speed (140 rpm). Through a dropping funnel 1.856 kg of benzaldehyde was added followed by 3.945 kg of sodium triacetoxyborohydride in five portions at $T_i$=20-25° C. according to the following addition order:

⅕ benzaldehyde (ca. 0.36 L);
stir for 5-10 minutes;
add ⅕ sodiumtriacetoxyborohydride (ca. 0.79 kg);
stir for 20-30 minutes;
repeat the procedure 4 times.

A sample was taken for in process control (IPC—for information only) and another 1.856 kg benzaldehyde was added through a dropping funnel followed by 3.946 kg sodium triacetoxy borohydride in five portions at $T_i$=20-25° C. according to the following addition order:

⅕ benzaldehyde (ca. 0.36 L);
stir for 5-10 minutes;
add ⅕ sodium triacetoxyborohydride (ca. 0.79 kg);
stir for 20-30 minutes;
repeat the procedure 4 times.

The mixture was left for at $T_i$=22.1° C. for 60 min.

The 250 L reactor was charged with 79.9 kg of water and stirred at 140 rpm, then 4.48 kg of sodium hydroxide was added and the mixture stirred at 140 rpm and $T_i$=24.8° C.; during 25 min to give a clear solution (exotherm). The sodium hydroxide solution was added with stirring at maximum speed (170 rpm) within 90 minutes at $T_i$=22.1-22.9° C. to the reaction mixture (weak exotherm and H$_2$ evolution at addition start) to give a faintly brown suspension. The suspension was stirred for 60 minutes at $T_i$=22.9-22.1° C. and 120 rpm, cooled to $T_i$=3.2° C., stirred for 16.5 h at this temperature at 120 rpm. The suspension was transferred to the centrifuge and centrifuged in one portion.

The 250 L reactor was charged with 19.3 kg of 2-propanol and 24.3 kg of water and cooled to $T_i$=3.5° C. The filter cake was washed with the cooled 2-propanol/water solution, the wet product (18.4 kg) was transferred into the tray dryer and dried for 2-3 days at $T_e$=55° C., p=400→1 mbar during 67 h 45 min). The dry product (14.08 kg—crude compound 2) was transferred into a poly drum with double in-liner, homogenised for 1 hour with 6 rpm at a mixing wheel and stored at ambient temperature under argon until further processing.

Stage 2: Crude (R)-5-(2-(benzylamino)ethyl)-1-(6,8-difluorochroman-3-yl)-1H-imidazole-2(3H)-thione hydrochloride A 400 L reactor was charged with 280.0 kg of water and stirred at $T_i$=16.0→21.0° C. and 120 rpm while 14.02 kg crude compound 2 was added at $T_i$=21-21.1° C. to give a suspension. To the suspension 5.28 kg of 37% HCl was added in 3 portions at $T_i$=21.1-22.0° C. during 23 min (weak exotherm), the mixture was heated to $T_i$=81.5° C. during 120 min and stirred at $T_i$=82.0° C. for 60 min, then cooled while stirring to $T_i$=47.1° C. within 150-180 minutes with a cooling rate of 0.2-0.25° C./min and stirred at medium speed at $T_i$=47.0° C. during 60 min. The suspension was centrifuged and filter cake washed with 64.5 kg water. The wet product (33.5 kg) was transferred into the tray dryer and dried at $T_e$=48→53° C.; p=300→1 mbar during 68 h 20 min. The dry product (12.40 kg) was transferred into a poly drum with double in-liner, homogenised for 3 hours with 13 rpm at a mixing wheel to give 12.4 kg (81%) of crude (R)-5-(2-(benzylamino)ethyl)-1-(6,8-difluorochroman-3-yl)-1H-imidazole-2(3H)-thione hydrochloride. Stored at ambient temperature under argon until further processing.

Stage 3: Purified (R)-5-(2-(benzylamino)ethyl)-1-(6,8-difluorochroman-3-yl)-1H-imidazole-2(3H)-thione hydrochloride A 400 L reactor was charged with 12.3 kg of crude (R)-5-(2-(benzylamino)ethyl)-1-(6,8-difluorochroman-3-yl)-1H-imidazole-2(3H)-thione hydrochloride, added 160.5 kg of toluene and the mixture was stirred at 130 rpm. Was added 98.0 kg of methanol and the mixture was heated to $T_i$=62° C. during 1 h and then slowly heated to reflux ($T_i$=65.9° C.). The solvent was removed by distillation (17.5-21 L/hours within 6-7 hours) and replaced simultaneously by toluene (17.5-21 L/hours within 6-7 hours). The reaction mixture was stirred for 45 minutes at 120 rpm at $T_i$=63.9° C., a faintly grey suspension resulted. The suspension was cooled to $T_i$=23.0° C. during 90 min, stirred at this temperature for 10 h (overnight).

The suspension was transferred into the centrifuge (filter cloth type: Lanz Anliker PP20) and centrifuged in one portion, the filter cake was washed with a mixture of 48.0 kg of toluene and 5.0 kg of methanol (premixed in a reactor at $T_i$=20-25° C. for 5-20 minutes). The wet product (17.8 kg) was filled into a poly drum with plastic in-liner under argon, transferred to the tray dryer (use plastic in-liners to avoid metal contact) and dried at $T_i$=48-53° C.; p=300→1 mbar for 67 h and then additionally dried at $T_e$=50° C.→53° C.; p=300→1 mbar for 47 h 20 min. The product (10.286 kg) was unloaded and filled into a 30 L poly drum with double plastic in-liner. The dry product (purified (R)-5-(2-(benzylamino)ethyl)-1-(6,8-difluorochroman-3-yl)-1H-imidazole-2(3H)-thione hydrochloride) was homogenised at a mixing wheel (7 rpm) for 2 hours and stored at ambient temperature under argon until further processing. (Purity by HPLC≥99.0%)

B. Preparation of compound 2 Amorphous Material

Three samples of compound 2 amorphous material were prepared by lyophilization using ~100 mg, ~500 mg and ~1 g of compound 2 lot 5. Solutions of the starting material were prepared in 1,4-dioxane at elevated temperature (~70-71° C.) at approximately 7 mg/mL. The solutions were then hot filtered using a 0.2 µm nylon filter and allowed to cool to ambient slowly by turning the heating device off. The ambient solutions were frozen on dry ice/acetone bath and transferred to a freeze dryer set at −50° C. and equipped with a vacuum pump. The samples generated at ~100 mg, ~500 mg scale of the starting material were dried for approximately 2 days. The sample prepared using ~1 g scale of the starting material was dried for ~5 days. After drying the resulting solids were stored in a freezer over a desiccant.

Experimental Details

1. Polymorph Screen—Medium Scale Experiments

Polymorph screen experiments were carried out primarily using lot 5 of compound 2 as starting material. Additional crystallization experiments were performed using three samples of amorphous material generated during the screen (sample nos. 1, 2 and 3). Experiments were carried out typically at ~10-80 mg. The solids produced were typically recovered by vacuum filtration and observed under polarized light.

a. Evaporation Experiments

Solutions of starting material were prepared at ambient by addition of a given solvent system to dissolve solids. The solutions were typically filtered using a 0.2 µm nylon filter. The solvents were removed using a rotary evaporator at ambient or elevated temperature (rotary evaporation, RE) or allowed to evaporate at ambient either from an open vial (fast evaporation, FE) or a vial covered with aluminum foil containing pinholes (slow evaporation, SE).

b. Fast, Slow and Crash Cooling Experiments

Samples of starting material were contacted with a given solvent system and brought to elevated temperature using an oil bath. The resulting solutions were typically hot filtered using a 0.2 µm nylon filter. The solutions were then either removed from the heating source to allow fast cooling to ambient temperature (FC), left on an oil bath with the heat device off for slow cooling to ambient temperature (SC) or placed on dry ice/acetone bath for crash cooling (CC). If the solids were not produced the solutions were typically sonicated and/or placed in a refrigerator or freezer.

c. Slurry Experiments

Solutions were prepared by addition of a solvent or solvent mixture to the starting material with excess solids present. The mixtures were then agitated in sealed vials at either ambient or a set temperature. For agitation at subambient temperature, chilled solvent was added and the sample was immediately transferred to a freezer. After a given amount of time, the solids were isolated.

d. Aqueous Vapor Stress Experiments

Samples of starting material were exposed to ~85% and ~97% relative humidity at ambient temperature and ~75% relative humidity at ~40° C. for a specified duration.

e. Organic Vapor Stress Experiments

Samples of starting material were exposed to vapors of a specified organic solvent for a given amount of time by placing open vials with solids tested into 20 mL vials containing solvent. Organic vapor stress experiments were conducted at ambient temperature.

f. Antisolvent Precipitation Experiments

Solutions of starting material were prepared at ambient or elevated temperature by addition of a minimum amount of a given solvent (S). The solutions were then either filtered/hot filtered directly into an excess of antisolvent (AS) or an antisolvent was rapidly added to filtered solutions. Precipitated solids were either immediately isolated or agitated. If the solids were not produced the solutions were typically sonicated and/or placed in a refrigerator or freezer.

g. Vapor Diffusion Experiments

Solutions of starting material were prepared at ambient temperature by addition of a minimum amount of an appropriate solvent. The samples were typically filtered using a 0.2 μm nylon filter. Open vials with filtered solutions were placed in 20 mL vials containing an appropriate antisolvent. The 20 mL vials were capped and left undisturbed.

h. Mechanical Stress Experiments

Samples of starting material were placed in a Retsch ball mill and milled for two five-minute cycles without solvent (dry grinding) or with a small amount of solvent added (wet grinding) scraping the solids between the cycles. Ten-minute cycles were used for milling of a selected sample without addition of solvent.

i. Heat Stress Experiments

Samples of amorphous material were placed in heating ovens at temperature set below or above the glass transition, or were agitated on a shaker block at elevated temperature for a given duration.

j. Slow Cooling of the Melt Experiment

Samples of amorphous material were heated on a hot plate at temperature above the glass transition. The sample was then allowed to slow cool to ambient by turning the heating device off.

2. Polymorph Screen—Well Plate Experiments (Non-cGMP)

Microscale experiments were carried out using a 96-well plate. The experiments were not conducted under cGMP conditions. The solids resulted were observed under polarized light.

Stock solutions of compound 2 lot 5 in hexafluoroisopropanol (~22 mg/mL) was prepared. 100 μL of the stock solution was added to each well of a microplate (~2.2 mg of compound 2 per well). Addition of a second and a third solvent was performed in the amount of 25 μL for each solvent. Addition of 50 μL of a second was performed when a third solvent was not used. Fast evaporation was allowed from wells that were left uncovered. For slow evaporation experiments, wells were covered using an aluminum foil pierced with one pinhole per well.

In the context of this specification, room temperature is the same as ambient temperature. Suitably, room temperature is a temperature between around 10° C. and around 35° C., preferably between around 15° C. and around 30° C., more preferably between around 20° C. and around 25° C.

Instrumental Techniques

3. X-ray Powder Diffraction (XRPD)

a. Inel

Selected XRPD patterns were collected with an Inel XRG-3000 diffractometer. An incident beam of Cu Kα radiation was produced using a fine-focus tube and a parabolically graded multilayer mirror. Prior to the analysis, a silicon standard (NIST SRM 640c) was analyzed to verify the Si 111 peak position. A specimen of the sample was packed into a thin-walled glass capillary, and a beam-stop was used to minimize the background from air. Diffraction patterns were collected in transmission geometry using Windif v. 6.6 software and a curved position-sensitive Equinox detector with a 2θ range of 120°. The data-acquisition parameters for each pattern are displayed in the "Brief Description of the Figures" section above.

b. Bruker

Selected XRPD patterns were collected using a Bruker D8 DISCOVER diffractometer and Bruker's General Area-Detector Diffraction System (GADDS, v. 4.1.20). An incident microbeam of Cu Kα radiation was produced using a long, fine-focus tube (40 kV, 40 mA), a parabolically graded multilayer mirror, and a 0.5 mm double-pinhole collimator. Prior to the analysis, a silicon standard (NIST SRM 640c) was analyzed to verify the Si 111 peak position. A specimen of the sample was packed between 3 μm thick films to form a portable, disc-shaped specimen. The prepared specimen was loaded in a holder secured to a translation stage. A video camera and laser were used to position the area of interest to intersect the incident beam in transmission geometry. The incident beam was scanned/and/or/rastered to optimize sampling and orientation statistics. A beam-stop was used to minimize the background from air. Diffraction patterns were collected using a HISTAR™ area detector located 15 cm from the sample and processed using GADDS. The intensity in the GADDS image of the diffraction pattern was integrated and displayed as a function of 2θ. The data-acquisition parameters for each pattern are displayed "Brief Description of the Figures" section above.

c. Bruker (Well Plate Holder)

XRPD patterns for microplate samples were collected using a Bruker D8 DISCOVER diffractometer and Bruker's General Area-Detector Diffraction System (GADDS, v. 4.1.20). An incident microbeam of Cu Kα radiation was produced using a long, fine-focus tube (40 kV, 40 mA), a parabolically graded multilayer mirror, and a 0.5 mm double-pinhole collimator. Prior to the analysis, a silicon standard (NIST SRM 640c) was analyzed to verify the Si 111 peak position. The samples were positioned for analysis by securing the well plate to a translation stage and moving each sample to intersect the incident beam in transmission geometry. The incident beam was scanned and rastered during the analysis to optimize orientation statistics. A beam-stop was used to minimize the background from air. Diffraction patterns were collected using a HISTAR™ area detector located 15 cm from the sample and processed using GADDS. The intensity in the GADDS image of the diffraction pattern was integrated and displayed as a function of 2θ. The instrument was operated under non-GMP conditions, and the results are non-GMP. The data-acquisition parameters for each pattern are displayed "Brief Description of the Figures" section above.

d. PANalytical

Selected XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640c) was analyzed to verify the Si 111 peak position. A specimen of the sample was sandwiched between 3 m-thick films and analyzed in transmission geometry. A beam-stop, short antiscatter extension, and typically a helium atmosphere were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data-acquisition parameters for each pattern are displayed in the "Brief Description of the Figures" section above including the divergence slit (DS) before the mirror and the incident-beam antiscatter slit (SS).

a. Indexing

Indexing and structure refinement are computational studies which are not performed under cGMP guidelines.

The XRPD pattern of compound 2 was indexed using proprietary software. The indexed solutions were verified and illustrated using CheckCell version Nov. 1, 2004. (LMGP-Suite Suite of Programs for the interpretation of X-ray Experiments, by Jean laugier and Bernard Bochu, ENSP/

Laboratoire des Matériaux et du Génie Physique, BP 46. 38042 Saint Martin d'Hères, France. WWW: http://www.inpg.fr/LMGP and http://www.ccp14.ac.uk/tutorial/lmgp/)

4. Thermogravimetric Analysis (TGA)

TG analyses were performed using a TA Instruments 2950 and Q5000 thermogravimetric analyzer. Temperature calibration was performed using nickel and Alumel™. Each sample was placed in an aluminum pan and inserted into the TG furnace. The furnace was heated under a nitrogen purge. The data acquisition parameters are displayed above each thermogram.

The method code for the thermogram (shown by the list of Figures in the "Brief Description of the Figures" section above) is an abbreviation for the start and end temperature as well as the heating rate; e.g., 25-350-10 means "from 25° C. to 350° C., at 10° C./min".

5. Correlated Thermogravimetric—Infrared Analysis (TG-IR)

Thermogravimetric infrared (TG-IR) analysis was performed on a TA Instruments thermogravimetric (TG) analyzer model 2050 interfaced to a Magna-IR 560® Fourier transform infrared (FT-IR) spectrophotometer (Thermo Nicolet) equipped with an Ever-Glo mid/far IR source, a potassium bromide (KBr) beamsplitter, and a mercury cadmium telluride (MCT-A) detector. The FT-IR wavelength verification was performed using polystyrene, and the TG calibration standards were nickel and Alumel™. The sample was placed in a platinum sample pan, and the pan was inserted into the TG furnace. The TG instrument was started first, immediately followed by the FT-IR instrument. The TG instrument was operated under a flow of helium at 90 and 10 cc/min. for the purge and balance, respectively. The furnace was heated under nitrogen at a rate of 20° C./minute to a final temperature of 250° C. IR spectra were collected approximately every 32 seconds for approximately 13 minutes. Each IR spectrum represents 32 co-added scans collected at a spectral resolution of 4 $cm^{-1}$. Volatiles were identified from a search of the High Resolution Nicolet Vapor Phase spectral library.

6. Differential Scanning Calorimetry (DSC)

DSC was performed using a TA Instruments 2920/or/Q2000 differential scanning calorimeter. Temperature calibration was performed using NIST traceable indium metal. The sample was placed into an aluminum DSC pan, covered with a lid, and the weight was accurately recorded. A weighed aluminum pan configured as the sample pan was placed on the reference side of the cell. The data acquisition parameters and pan configuration for each thermogram are displayed in the image of each of the thermograms.

The method code on the thermogram is an abbreviation for the start and end temperature as well as the heating rate; e.g., 25-250-10 means "from 25° C. to 250° C., at 10° C./min".

7. Cycling Differential Scanning Calorimetry (cycling DSC)

For studies of the glass transition temperature ($T_g$) of amorphous material, the sample cell was equilibrated at −50° C., then heated under nitrogen at a rate of 20° C./min up to 70° C. and equilibrated at this temperature. The sample cell was then allowed to cool and equilibrate at −50° C. It was again heated at a rate of 20° C./min to a final temperature of 250° C. The $T_g$ is reported from the half-height of the transition (inflexion point).

8. Hotstage Microscopy (HSM)

Hotstage microscopy was performed using a Linkam hotstage (FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20× objective with crossed polarizers and a first order red compensator. Images were captured using SPOT software (v. 4.5.9).

9. Moisture Sorption Analysis

Moisture sorption/desorption data were collected on a VTI SGA-100 Vapor Sorption Analyzer. NaCl and PVP were used as calibration standards. Samples were not dried prior to analysis. Sorption and desorption data were collected over a range from 5 to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

10. Proton Solution Nuclear Magnetic Resonance Spectroscopy ($^1$H NMR)

All samples were prepared in deuterated DMSO. The specific acquisition parameters are listed on the "Brief Description of the Figures" section above in FIG. 8A.

Characterisation data for lots 1, 2, 3, 4, 6 and 5 of compound 2 are summarized in Table 5.

TABLE 5

Physical Characterisation of compound 2 Materials

| Sample | Analytical Technique | Results |
| --- | --- | --- |
| Lot 1 (sample no. 4) | XRPD (high resolution) | Crystalline, designated as Form A of compound 2 |
| | TGA | Sharp weight loss at ~258° C. (onset) |
| | DSC | Sharp endo at ~191.4° C. (onset) with peak max at ~193.2° C. Heat of fusion ~141.7 J/g |
| Lot 2 (sample no. 5) | XRPD (high resolution) | Crystalline, designated as Form A of compound 2 |
| | TGA | ~0.6 wt % loss between ~185° C. and ~200° C. Sharp weight loss at ~257° C. (onset) |
| | DSC | Sharp endo at ~191.7° C. (onset) with peak max at ~193.0° C. Heat of fusion ~139.8 J/g |
| Lot 3 (sample no. 6) | XRPD (high resolution) | Crystalline, designated as Form B of compound 2 |
| | TGA | ~2.3 wt % loss between ~162° C. and ~200° C. Sharp weight loss at ~260° C. (onset) |
| | DSC | Slightly asymmetric, sharp endo at ~189.5° C. (onset) with peak max at ~191.9° C. Heat of fusion ~140.6 J/g |

TABLE 5-continued

Physical Characterisation of compound 2 Materials

| Sample | Analytical Technique | Results |
|---|---|---|
| | NMR | Consistent with compound 2 chemical structure |
| | | Contains ~0.13 moles of ethyl acetate based on peaks at ~4.03 ppm, ~1.99 ppm and ~1.18 ppm |
| | | Small unidentified peaks at ~9.87 ppm, ~5.31 ppm, ~4.09 ppm, and ~3.17 ppm[a] |
| Lot 4 (sample no. 7) | XRPD (high resolution) | Crystalline, designated as Form A of compound 2 |
| | TGA | Sharp weight loss at ~258° C. (onset) |
| | DSC | Sharp endo at ~191.9° C. (onset) with peak max at ~193.5° C. Heat of fusion ~138.7 J/g |
| Lot 6 (sample no. 8) | XRPD (high resolution) | Crystalline, designated as Form A of compound 2 |
| | TGA | Sharp weight loss at ~262° C. (onset) |
| | DSC | Sharp endo at ~192.0° C. (onset) with peak max at ~193.8° C. Heat of fusion ~139.8 J/g |
| Lot 5 (sample no. 9) | XRPD (high resolution) | Crystalline, designated as Form A of compound 2 |
| | TGA | Sharp weight loss at ~259° C. (onset) |
| | DSC | Sharp endo at ~192.0° C. (onset) with peak max at ~192.6° C. Heat of fusion ~147.1 J/g |
| | HSM | 24.4° C. - Initial, birefringent with extinction |
| | | 143.0° C. - No change noted |
| | | 187.9° C. - Solid-liquid transition began |
| | | 189.2° C. - During solid-liquid transition |
| | | 192.2° C. - Solid-liquid transition complete. Cooling (uncontrolled) |
| | | 35.6° C. - No recrystallization observed |
| | Moisture sorption | Negligible loss upon equilibration at ~5% RH |
| | | ~0.02 wt % gain between ~5% and ~75% RH |
| | | ~0.19 wt % gain between ~75% and ~95% RH |
| | | ~0.20 wt % loss between ~95% and ~5% RH. Small hysteresis between ~85% and ~45% RH upon desorption |

[a] Peaks at ~2.5 ppm and ~3.3 ppm are due to partially deuterated DMSO and water, respectively The materials were characterised by high resolution X-ray powder diffraction (XRPD), thermogravimetry (TGA), and differential scanning calorimetry (DSC). Hotstage microscopy and moisture sorption analysis was performed on lot 5. Lot 3 was additionally characterised by proton nuclear magnetic resonance spectroscopy ($^1$H NMR). The XRPD pattern of lot 4 was indexed. No attempt at molecular packing was performed to confirm the tentative indexing solution.

A tentative indexing solution for lot 4 is illustrated in FIG. 1. Space groups consistent with the assigned extinction symbol, unit cell parameters, and derived quantities are presented in Table 6.

TABLE 6

Tentative Indexing Solution and Derived Quantities for compound 2 Materials

| Form/Pattern | Form A (lot 4) | Form B (lot 3) |
|---|---|---|
| Family and Space Group | Triclinic P1 (#1) | Triclinic P1 (#1) |
| Z'/Z | 2/2 | 2/2 |
| a (Å) | 7.664 | 7.677 |
| b (Å) | 11.208 | 11.216 |
| c (Å) | 11.581 | 11.590 |
| α (deg)[a] | 100.16 or 79.84 | 100.19 or 79.81 |
| β (deg)[a] | 102.06 or 77.94 | 102.29 or 77.71 |
| γ (deg) | 90.00 | 90.00 |
| Volume (Å$^3$/cell) | 956.8 | 959.0 |
| V/Z (Å$^3$/asym. unit) | 478.4 | 479.5 |
| Assumed Composition[b] | $C_{21}H_{21}F_2N_3OS$ | $C_{21}H_{21}F_2N_3OS$ |
| Density (g/cm$^3$)[b] | 1.394 | 1.390 |
| Weight Fraction Solvent (%)[b] | N/A | N/A |

Overall, the data for lots 1, 4, 6 and 5 indicate that the materials are unsolvated and composed primarily of the same solid form designated as Form A. The data for lot 3 are consistent with a non-stoichiometric ethyl acetate solvate of compound 2, designated as Form B. Lot 2 is consistent with Form A based on XRPD, however, some degree of solvation is suggested for the material based on TGA. The six lots, overall, are composed primarily of a single crystalline phase.

The XRPD pattern exhibited by lot 4 was successfully indexed indicating that the material is composed primarily of a single crystalline phase (Table 6). Agreement between the allowed peak positions and the observed peaks points out a consistent unit cell determination (FIG. 1). Two angles are provided for the α and β angles. Should the γ angle be slightly less than 90°, then the acute angles should be used for α and β. When the γ angle is slightly greater than or equal to 90°, the obtuse angles should be used for α and β. Both the acute and non-acute cells were given since the γ angle refined to 90.00° but could be hundredths of a degree below 90° within the error.

Thermogravimetric (TGA) curves for lots 1, 4, 6 and 5 were similar and showed no weight losses below ~257-262° C., indicating that the materials are unsolvated. Lot 3, however, exhibited a ~2.3 wt % loss between ~162° C. and ~200° C. associated with the release of ~0.13 moles of ethyl acetate based on NMR data for the lot and TG-IR data acquired on the material generated during the screen. The high temperature of the release suggests incorporation of the solvent within the crystal lattice. Similar but less pronounced differences were observed upon heating of lot 2. The material displayed a smaller weight loss (~0.6 wt %) between ~185° C. and ~200° C. Sharp weight losses were observed at ~257-262° C. for the six lots attributable to decomposition of the materials.

The DSC thermograms obtained on the lots 1 to 5 exhibited sharp endotherms in the ~191.9-193.8° C. range (peak maxima) consistent with melting, as confirmed by hotstage microscopy data acquired on lot 5. A slight asymmetry of the endotherm displayed by lot 3 was observed, possibly due to overlapping with a desolvation event, as suggested by TGA data, as well as NMR data showing the presence of ethyl acetate in the material.

Hotstage microscopy data were acquired on lot 5 used as primary starting material for the polymorph screen. The material initially showed birefringence with extinction, indicative of its crystallinity. No visual changes were seen upon heating below ~143.0° C. A solid-liquid transition was observed in the temperature range of ~187.9-192.2° C. indicating melting of the material. No crystallization was seen upon cooling to ~35.6° C.

Moisture sorption analysis data were acquired on lot 5. The data are consistent with a material of low hygroscopicity. The material showed a negligible weight loss upon equilibration at ~5% RH. A negligible gain (~0.02 wt %) was observed below ~75% RH, above which the material gained additional ~0.19 wt %, with a total water uptake of ~0.21 wt % between ~5% and ~95% RH. Nearly complete desorption occurred with a small hysteresis between ~85% and ~45% RH upon decreasing the relative humidity (~0.20 wt % loss between ~95% and ~5% RH).

A proton NMR spectrum was acquired on lot 3 to help understand the differences observed for the material compared to other lots. The NMR chemical shifts and integral values for the material are consistent with the chemical structure of compound 2. The spectrum exhibited additional peaks at ~4.03 ppm, ~1.99 ppm and ~1.18 ppm attributable to ~0.13 moles of ethyl acetate, the presence of which would be expected based on generation conditions. Small unidentified peaks were also observed at ~9.87 ppm, ~5.31 ppm, ~4.09 ppm, and ~3.17 ppm likely due to the presence of impurities.

C. Polymorph Screen of Compound 2

Isolated solids were analyzed by X-ray powder diffraction (XRPD), and the patterns were compared to each other and to the XRPD pattern of lot 5 designated as Form A. The pattern acquired on lot 3 and designated as Form B was also used as reference.

The conditions and results of microscale and medium scale crystallization experiments performed in organic solvents using lot 5 of compound 2 are summarized in Table 7 and Table 8, respectively. Table 9 presents results of organic vapor and mechanical stress of the material.

Each of the following processes that results in Form A of compound 2 is another aspect of the present invention, and each of the following processes that results in Form B of compound 2 is another aspect of the present invention.

TABLE 7

Crystallization of compound 2 from Organic Solvents using Lot 5 (Form A) (Microscale Evaporation)

| Well | Conditions[a] | Microscope Observation | XRPD Results |
|---|---|---|---|
| A1 | HFIPA/Acetone/1,4-Dioxane, 100/25/25 | UM, some BE | Form A |
| A2 | HFIPA/Acetone/EtOH, 100/25/25 | UM, some BE | Form A |
| A3 | HFIPA/Acetone/Heptane, 100/25/25 | UM, some BE | Form A |
| A4 | HFIPA/Acetone/IPA, 100/25/25 | UM, some BE | Form A |
| A5 | HFIPA/Acetone/IPE, 100/25/25 | UM, some BE | Form A |
| A6 | HFIPA/Acetone/MeOH, 100/25/25 | UM, some BE | Form A |
| A7 | HFIPA/Acetone/MCH, 100/25/25 | UM, some BE on single part. | Form A |
| A8 | HFIPA/Acetone/Nitromethane, 100/25/25 | UM, some BE on single part. | Form A |
| A9 | HFIPA/Acetone/MTBE, 100/25/25 | UM, some BE on single part. | Form A |
| A10 | HFIPA/Acetone/Water, 100/25/25 | UM, no BE | Form A |
| A11 | HFIPA/Acetone/TFE, 100/25/25 | UM, some BE | Form A |
| A12 | HFIPA/Acetone, 100/50 | UM, some BE | Form A |
| B1 | HFIPA/ACN/1,4-Dioxane, 100/25/25 | UM, very few part. w/ some BE | Form A |
| B2 | HFIPA/ACN/EtOH, 100/25/25 | UM, very few part. w/ some BE | Form A |
| B3 | HFIPA/ACN/Heptane, 100/25/25 | UM, no BE | Form A |
| B4 | HFIPA/ACN/IPA, 100/25/25 | UM, no BE | Form A |
| B5 | HFIPA/ACN/IPE, 100/25/25 | UM, very few part. w/ some BE | Form A |
| B6 | HFIPA/ACN/MeOH, 100/25/25 | UM, no BE | Form A |
| B7 | HFIPA/ACN/MCH, 100/25/25 | UM, no BE | Form A |
| B8 | HFIPA/ACN/Nitromethane, 100/25/25 | UM, no BE | Form A |
| B9 | HFIPA/ACN/MTBE, 100/25/25 | UM, no BE | Form A |
| B10 | HFIPA/ACN/Water, 100/25/25 | UM, very few part. w/ some BE | Form A |
| B11 | HFIPA/ACN/TFE, 100/25/25 | UM, no BE | Form A |
| B12 | HFIPA/ACN, 100/50 | UM, no BE | Form A |
| C1 | HFIPA/CHCl$_3$/1,4-Dioxane, 100/25/25 | UM, no BE | Form A |
| C2 | HFIPA/CHCl$_3$/EtOH, 100/25/25 | UM, no BE | Form A |
| C3 | HFIPA/CHCl$_3$/Heptane, 100/25/25 | UM, no BE | Form A |
| C4 | HFIPA/CHCl$_3$/IPA, 100/25/25 | UM, no BE | Form A |
| C5 | HFIPA/CHCl$_3$/IPE, 100/25/25 | UM, very few part. w/ some BE | Form A |
| C6 | HFIPA/CHCl$_3$/MeOH, 100/25/25 | UM, no BE | Form A |
| C7 | HFIPA/CHCl$_3$/MCH, 100/25/25 | UM, no BE | Form A + peak[b] |
| C8 | HFIPA/CHCl$_3$/Nitromethane, 100/25/25 | UM, no BE | Form A |
| C9 | HFIPA/CHCl$_3$/MTBE, 100/25/25 | UM, no BE | Form A |
| C10 | HFIPA/CHCl$_3$/Water, 100/25/25 | UM, no BE | Form A |
| C11 | HFIPA/CHCl$_3$/TFE, 100/25/25 | UM, no BE | Form A |
| C12 | HFIPA/CHCl$_3$, 100/50 | UM, no BE | Form A |
| D1 | HFIPA/EtOAc/1,4-Dioxane, 100/25/25 | UM, no BE | Form A |
| D2 | HFIPA/EtOAc/EtOH, 100/25/25 | UM, no BE | Form A |
| D3 | HFIPA/EtOAc/Heptane, 100/25/25 | UM, no BE | Form A |
| D4 | HFIPA/EtOAc/IPA, 100/25/25 | UM, no BE | Form A |
| D5 | HFIPA/EtOAc/IPE, 100/25/25 | UM, no BE | Form A |
| D6 | HFIPA/EtOAc/MeOH, 100/25/25 | UM, no BE | Form A |
| D7 | HFIPA/EtOAc/MCH, 100/25/25 | UM, no BE | Form A |

TABLE 7-continued

Crystallization of compound 2 from Organic Solvents using Lot 5 (Form A) (Microscale Evaporation)

| Well | Conditions[a] | Microscope Observation | XRPD Results |
|---|---|---|---|
| D8 | HFIPA/EtOAc/TFE, 100/25/25 | UM, no BE | Form A |
| D9 | HFIPA/EtOAc/MTBE, 100/25/25 | UM, no BE | Form A |
| D10 | HFIPA/EtOAc/Water, 100/25/25 | UM, no BE | Form A |
| D11 | HFIPA/EtOAc/MTBE, 100/25/25 | UM, no BE | Disordered |
| D12 | HFIPA/EtOAc, 100/50 | UM, no BE | Form A |
| E1 | HFIPA/MEK/1,4-Dioxane, 100/25/25 | UM, no BE | Form A |
| E2 | HFIPA/MEK/EtOH, 100/25/25 | UM, no BE | Disordered |
| E3 | HFIPA/MEK/Heptane, 100/25/25 | UM, no BE | Disordered |
| E4 | HFIPA/MEK/IPA, 100/25/25 | UM, no BE | Disordered |
| E5 | HFIPA/MEK/IPE, 100/25/25 | UM, no BE | Disordered |
| E6 | HFIPA/MEK/MeOH, 100/25/25 | UM, no BE | Disordered |
| E7 | HFIPA/MEK/MCH, 100/25/25 | UM, no BE | Disordered |
| E8 | HFIPA/MEK/Nitromethane, 100/25/25 | UM, no BE | Disordered |
| E9 | HFIPA/MEK/MTBE, 100/25/25 | UM, no BE | Disordered |
| E10 | HFIPA/MEK/Water, 100/25/25 | UM, no BE | Disordered |
| E11 | HFIPA/MEK/TFE, 100/25/25 | UM, no BE | Disordered |
| E12 | HFIPA/MEK, 100/50 | UM, no BE | Disordered |
| F1 | HFIPA/THF/1,4-Dioxane, 100/25/25 | UM, no BE | Disordered |
| F2 | HFIPA/THF/EtOH, 100/25/25 | UM, no BE | Form A |
| F3 | HFIPA/THF/Heptane, 100/25/25 | UM, no BE | Form A |
| F4 | HFIPA/THF/IPA, 100/25/25 | UM, no BE | Disordered |
| F5 | HFIPA/THF/IPE, 100/25/25 | UM, no BE | Form A |
| F6 | HFIPA/THF/MeOH, 100/25/25 | UM, no BE | Form A |
| F7 | HFIPA/THF/MCH, 100/25/25 | UM, no BE | Form A |
| F8 | HFIPA/THF/Nitromethane, 100/25/25 | UM, no BE | Form A |
| F9 | HFIPA/THF/MTBE, 100/25/25 | UM, no BE | Form A |
| F10 | HFIPA/THF/Water, 100/25/25 | UM, no BE | Form A |
| F11 | HFIPA/THF/TFE, 100/25/25 | UM, no BE | Form A |
| F12 | HFIPA/THF, 100/50 | UM, no BE | Disordered |
| G1 | HFIPA/Toluene/1,4-Dioxane, 100/25/25 | UM, no BE | Form A |
| G2 | HFIPA/Toluene/EtOH, 100/25/25 | UM, no BE | Form A |
| G3 | HFIPA/Toluene/Heptane, 100/25/25 | UM, no BE | Form A |
| G4 | HFIPA/Toluene/IPA, 100/25/25 | UM, very few part. w/ some BE | Form A |
| G5 | HFIPA/Toluene/IPE, 100/25/25 | UM, no BE | Form A |
| G6 | HFIPA/Toluene/MeOH, 100/25/25 | UM, no BE | Form A |
| G7 | HFIPA/Toluene/MCH, 100/25/25 | UM, very few part. w/ some BE | Form A |
| G8 | HFIPA/Toluene/Nitromethane, 100/25/25 | Film | No peaks |
| G9 | HFIPA/Toluene/MTBE, 100/25/25 | UM, no BE | Form A |
| G10 | HFIPA/Toluene/Water, 100/25/25 | UM, no BE | Form A |
| G11 | HFIPA/Toluene/TFE, 100/25/25 | UM, no BE | Form A |
| G12 | HFIPA/Toluene, 100/50 | UM, no BE | Form A |
| H1 | HFIPA/DCM/1,4-Dioxane, 100/25/25 | UM, no BE | Form A |
| H2 | HFIPA/DCM/EtOH, 100/25/25 | UM, no BE | Form A |
| H3 | HFIPA/DCM/Heptane, 100/25/25 | UM, no BE | Form A |
| H4 | HFIPA/DCM/IPA, 100/25/25 | UM, no BE | Form A |
| H5 | HFIPA/DCM/IPE, 100/25/25 | UM, no BE | Form A |
| H6 | HFIPA/DCM/MeOH, 100/25/25 | UM, no BE | Form A |
| H7 | HFIPA/DCM/MCH, 100/25/25 | UM, no BE | Form A |
| H8 | HFIPA/DCM/Nitromethane, 100/25/25 | Film | No peaks |
| H9 | HFIPA/DCM/MTBE, 100/25/25 | UM, no BE | Form A |
| H10 | HFIPA/DCM/Water, 100/25/25 | UM, no BE | Form A |
| H11 | HFIPA/DCM/TFE, 100/25/25 | UM, no BE | Form A |
| H12 | Blank | — | — |

[a]X/Y/Z, x/y/z: x μl of solution X (compound 2 lot 5 in HFIPA, 3981-84-01), y μl of solvent Y, and z μl of solvent Z were consecutively added to each well (sample no. 9). Slow evaporation was allowed for rows A through D. Fast evaporation was allowed for rows E through H

[b]One peak present not apparent in other XRPD patterns for Form A but consistent with Form A based on indexing solution for the material.

HFIPA—hexafluoroisopropanol;

ACN—acetonitrile;

MTBE—methyl tert-butyl ether;

IPA—isopropyl alcohol;

IPE—isopropyl ether;

MCH—methylcyclohexane;

TFE—2,2,2-Trifluoroethanol;

EtOAc—ethyl acetate;

MEK—methyl ethyl ketone;

DCM—dichloromethane;

UM—unknown morphology;

BE—Birefringence and extinction;

w/—with;

part.—particle/particles.

TABLE 8

Crystallization of compound 2 from Organic Solvents using Lot 5 (Form A) (Medium Scale)

| Solvent[a] (X/Y) | Conditions[b] | Sample No. | Analytical Technique | Results |
|---|---|---|---|---|
| Acetone | Slurry, RT, 5 days | 11 | XRPD OM | Form A UM, BE |
| Acetone/toluene | S/AS attempt. Hot soln. at 70° C. into RT AS (clear). Kept at −25 to −10° C., 6 days | 12 | XRPD OM | Form A White, fine needles, BE |
| ACN | Slurry, 60° C., 3 days | 13 | XRPD OM | Form A UM, agglom., BE on smaller part. |
| Dioxane | Lyophilization, −50° C. (Diss. at 71° C., SC to RT) | 14 | XRPD OM | No peaks UM, no BE |
| DMF/ACN | S/AS attempt. AS into soln (clear), sonic. (clear). Kept at −25 to −10° C., 1 week | 15 | XRPD OM | Form A Bladed part., agglom., BE |
| DMF/ACN | VD, RT | 16 | — | No solids |
| DMF/DEE | VD, RT | 17 | — | No solids |
| DMF/EtOAc | S/AS attempt. AS into soln (clear), sonic. (clear). Kept at −25 to −10° C. | 18 | — | No solids |
| DMSO/ACN (1/1) | FC attempt from 70° C. to RT (clear), sonic. (clear). Kept at 2-8° C., 1 day | 19 | XRPD OM | Form A UM, agglom., some BE on single part. |
| DMSO/MeOH | S/AS attempt. AS into soln (clear), sonic. (clear). Kept at 2-8° C. | 20 | XRPD OM | Form A Plate-like, BE |
| DMSO/MTBE | VD, RT | 21 | — | No solids |
| DMSO/toluene | S/AS attempt. AS into soln (clear), sonic. (clear). Kept at 2-8° C. | 22 | — | No solids |
| CHCl$_3$ | Slurry, RT, 5 days | 23 | XRPD OM | Form A UM, BE |
| EtOAc | Slurry, 50° C., 3 days | 24 | XRPD OM | Form A UM, some agglom., BE |
| EtOAc | From sample no. 1.[c] Slurry, RT, 3 days | 25 | XRPD OM | Form A UM, no BE |
| HFIPA | RE, RT to 40° C. | 1 | XRPD OM | No peaks Opaque to glassy, no BE |
| HFIPA/CHCl$_3$ | VD, RT | 26 | — | No solids |
| HFIPA/IPE | S/AS attempt. AS into soln. (clear), sonic. (clear). PSE | 27 | XRPD OM | Form A Elongated particles, agglom., BE |

[a](X/Y) = Approximate ratio of solvents by volume.
[b]Temperature and duration of experiments are approximate
[c]Starting material, a potentially amorphous material, exhibited no peaks in its XRPD pattern

| Solvent[a] (X/Y) | Conditions[b] | Sample No. | Analytical Technique | Results |
|---|---|---|---|---|
| IPA | Slurry, 60° C., 3 days | 28 | XRPD OM | Form A UM, agglom., BE on smaller part. |
| IPA/DMSO (2.5/1) | SC attempt from 70° C. to RT, sonic. (clear) Solids in 1 week | 29 | XRPD OM | Form A Platy, agglom., BE |
| MEK | Slurry, 50° C., 3 days | 30 | XRPD OM | Form A UM, agglom., BE on smaller part. |
| MEK | FC attempt from 70° C. to RT (clear), sonic. | 31 | — | No solids |
| MEK | CC (dry ice/acetone) attempt from 70° C. (few ppt). Kept on dry ice/acetone, 2 hr. Kept at −25 to −10° C., 1 day. RE, ~½ vol., 50° C. Kept at −25° C. to −10° C., 1 week[c] | 32 | XRPD OM | Form A UM, agglom., BE on smaller non-agglom. Part. |
| — | Filtrate from sample no. 32 RE, ~½ vol., 40° C. Kept at −25 to −10° C., 2 weeks | 33 | XRPD OM | Form A Granule-like, very small part. w/ BE |
| MEK/heptane | From sample no. 31 S/AS. AS into soln (cloudy), standing, 1 day (ppt) | 34 | XRPD OM | Form A UM, fine part., no BE |
| MEK/toluene (3/1) | Slurry, 68° C., 9 days | 35 | XRPD OM | Form A Plate-like, BE |
| MEK/toluene (4/1) | FC attempt from 70° C. to RT (clear), sonic. (clear). Kept at −25 to −10° C., 4 days[d] | 36 | XRPD OM | Material D (disordered) Platy, BE |

TABLE 8-continued

| | | | | |
|---|---|---|---|---|
| MEK/toluene (4/1) | FC attempt from 70° C. to RT (clear). Kept at −25 to −10° C., 5 days | 37 | XRPD OM | Form A Off-white, fine particles, BE |
| MeOH/CHCl₃ (1/1) | Slurry, RT, 5 days | 38 | XRPD OM | Form A UM, agglom., BE on smaller part. |
| MeOH/DMF (~2/1) | CC attempt (dry ice/IPA) from 59° C. (clear), sonic. (clear). Kept at −25 to −10° C. | 39 | — | No solids |
| Nitromethane | Slurry, 60° C., 3 days | 40 | XRPD OM | Form A UM, agglom., BE on smaller part. |
| TFE, | Slurry, RT, 5 days | 41 | XRPD OM | Form A UM, BE |
| TFE | FE | 42 | XRPD OM | Form A UM, agglom., opaque, no BE + UM, BE |
| TFE | SC from 70° C. to RT (clear), sonic. (cloudy then ppt) | 43 | XRPD OM | Form A UM, agglom., some BE on single part. |
| THF | Slurry, RT, 5 days | 44 | XRPD OM | Form A UM, agglom., BE on smaller part. |
| THF | FE | 45 | XRPD OM | Form A (disordered) UM, agglom., no BE |
| THF | FC attempt from 55° C. to RT, sonic. | 46 | — | No solids |
| THF/CHCl₃ (1/4) | SC attempt from 58° C. to RT (clear). Kept at −25 to −10° C., 4 days | 47 | XRPD OM | Form A UM, agglom., no BE |
| THF/EtOAc | Diss. in THF at 50° C. FC to RT. Add. EtOAc (clear). Partial RE (some ppt). Left at RT, overnight | 48 | XRPD OM | Form B Off-white, irregular small plates, BE |
| THF/EtOH (1/1) | Slurry, RT, 5 days | 49 | XRPD OM | Form A UM, agglom., BE on smaller part. |
| THF/heptane | From sample no. 46 S/AS. AS into soln (ppt, sticky solids), sonic. | 50 | XRPD OM | Form A UM, no BE |
| Toluene | Slurry, 60° C., 3 days | 51 | XRPD OM | Form A UM, agglom., BE on smaller part. |

[a](X/Y) = Approximate ratio of solvents by volume.
[b]Temperature and duration of experiments are approximate
[c]Performed at ~500 mg scale in the attempt to scale up Material D at subambient conditions
[d]Solids formed at subambient temperature were observed to dissolve at ambient and repricipitated when returned to subambient temperature. The material was vacuum filtered while cold immediately upon removal from freezer DMSO—dimethyl sulfoxide;
DEE—Diethyl ether;
DMF—dimethylformamide;
RT—room temperature;
diss.—dissolution/dissolved;
add.—addition/added;
agglom.—agglomerates;
ppt—precipitation;
soln.—olution/solutions;
S/AS—solvent/antisolvent precipitation;
OM—optical microscopy;
VD—vapor diffusion;
PSE—partial slow evaporation.

TABLE 9

Organic Vapor Stress and Mechanical Stress of compound 2 using Lot 5 (Form A)

| Conditions[a] | Sample No. | Analytical Technique | Results |
|---|---|---|---|
| EtOAc, vapor stress, 11 days | 52 | XRPD OM | Form A Plate-like, BE |
| CHCl₃, vapor stress, 11 days | 53 | XRPD OM | Form A Plate-like, agglom., BE on non-agglom. part. |
| Dry grinding, 2 × 5 min. cycles, scraped between cycles | 54 | XRPD OM | Form A (disordered) UM, no BE |

TABLE 9-continued

Organic Vapor Stress and Mechanical Stress
of compound 2 using Lot 5 (Form A)

| Conditions[a] | Sample No. | Analytical Technique | Results |
|---|---|---|---|
| Dry grinding, 2 × 10 min. cycles, scraped between cycles | 55 | XRPD<br>OM | Form A (disordered)<br>UM, no BE |
| Acetone, wet grinding, 2 × 5 min. cycles, scraped between cycles | 56 | XRPD<br>OM | Form A<br>UM, very few part. w/ BE |
| DMF, wet grinding, 2 × 5 min. cycles, scraped between cycles | 57 | XRPD<br>OM | Form A<br>UM, very few part. w/ BE |
| MEK, wet grinding, 2 × 5 min. cycles, scraped between cycles | 58 | XRPD<br>OM | Form A<br>UM, very few part. w/ BE |
| THF, wet grinding, 2 × 5 min. cycles, scraped between cycles | 59 | XRPD<br>OM | Form A<br>UM, no BE |
| TFE, wet grinding, 2 × 5 min. cycles, scraped between cycles | 60 | XRPD<br>OM | Form A<br>UM, very few part. w/ BE |

[a]Duration of experiments is approximate

The conditions and results of crystallization in non-aqueous media, organic vapor stress and heat stress using various samples of compound 2 amorphous as starting material are presented in Table 10, Table 11 and Table 12, correspondingly.

TABLE 10

Crystallization of compound 2 from Organic Solvents using Amorphous Material

| Solvent[a] (X/Y) | Conditions[b] | Sample No. | Analytical Technique | Results |
|---|---|---|---|---|
| ACN | Spontaneous ppt, slurry, 50° C., 6 days | 61 | XRPD<br>OM | Form A[e]<br>UM, agglom., some BE on smaller part. |
| Heptane | Slurry, 50° C., 6 days | 62 | XRPD<br>OM | Form A[e]<br>UM, agglom., some BE |
| IPA | Spontaneous ppt, slurry, 50° C., 6 days | 63 | XRPD<br>OM | Form A[e]<br>UM, agglom., no BE + rosette-like, BE |
| MCH[c] | Slurry, 35° C., 1 day | 64 | XRPD<br>OM | Form A[e]<br>UM, agglom., no BE |
| MEK | Spontaneous ppt, slurry, RT, 6 days | 65 | XRPD<br>OM | Form A[e]<br>UM, agglom., no BE |
| MEK[d] | FE | 66 | XRPD<br>OM | No peaks<br>Majority opaque no BE + very few w/ BE |

[a](X/Y) = Approximate ratio of solvents by volume
[b]Starting material - sample no. 2 unless otherwise indicated. Temperature and duration of experiments are approximate
[c]Starting material - sample no. 3
[d]Starting material - sample no. 14
[e]Minor peak shifts are attributable to the X-ray instrument used

| Solvent[a] (X/Y) | Conditions[b] | Sample No. | Analytical Technique | Results |
|---|---|---|---|---|
| MEK[c,d] | Agitation-slurry, −25 to −10° C., 1 day | 67 | XRPD<br>OM | Form A<br>UM, agglom., single part. w/ BE |
| MEK/toluene (4/1)[c] | Slurry, RT, 5 days.<br>Washed w/ MEK/toluene (4/1) | 68 | XRPD<br>OM | Form A[e]<br>Off-white, fine particles, no BE |
| MeOH | Spontaneous ppt, slurry, RT, 6 days | 69 | XRPD<br>OM | Form A[e]<br>UM, agglom., some BE on smaller part. |
| MTBE | Spontaneous ppt, slurry, RT, 6 days | 70 | XRPD<br>OM | Form A[e]<br>UM, agglom., no BE |
| Nitromethane[c] | Initially clear then spontaneous ppt, slurry, 35° C., 1 days | 71 | XRPD<br>OM | Form A[e]<br>UM, agglom., no BE |
| TFE[c] | Initially slightly cloudy, slurry, RT, 1 day (ppt) | 72 | XRPD<br>OM | Form A[e]<br>UM, agglom., some BE |
| THF | Initially clear then spontaneous ppt, slurry, RT, 3 days (clear). FE (film, scraped, solids) | 73 | XRPD<br>OM | X-ray amorphous<br>UM, opaque, no BE |

TABLE 10-continued

| | | | | |
|---|---|---|---|---|
| Toluene | Initially clear then spontaneous ppt, slurry, 50° C., 6 days | 74 | XRPD OM | Form A[e] Needles, agglom., some BE |
| Toluene[c,d] | Agitation-slurry, −25 to −10° C., 1 day | 75 | XRPD OM | Form A UM, agglom., single part. w/ BE |

[a](X/Y) = Approximate ratio of solvents by volume

TABLE 11

Organic Vapor Stress of compound 2 Amorphous Material

| Conditions[a] | Sample No. | Analytical Technique | Results |
|---|---|---|---|
| IPE, 2 days[b] | 76 | XRPD OM | Form A Needle-like, agglom., some BE |
| Acetone, 1 day | 77 | XRPD OM | Form A UM, agglom., single part. w/ BE |
| CHCl$_3$, 1 day | 78 | XRPD OM | Form A UM, agglom., single part. w/ BE |
| EtOAc, 1 day | 79 | XRPD OM | Form B UM, agglom., single part. w/ BE |

[a]Starting material - sample no. 2 unless otherwise indicated. Duration of experiments is approximate
[b]Starting material - sample no. 3

TABLE 12

Heat Stress of compound 2 Amorphous Material and Cooling from the Melt

| Conditions[a] | Sample No. | Analytical Technique | Results |
|---|---|---|---|
| 36° C., 1 day[b] | 80 | XRPD OM | Disordered, Form A UM, agglom., no BE |
| 40° C., 3 hrs | 81 | XRPD OM | Amorphous/Form A mixture UM, agglom., no BE |
| 50° C., 3 hrs | 82 | XRPD OM | Amorphous/Form A mixture UM, agglom., opaque, no BE |
| 60° C., 3 hrs | 83 | XRPD OM | Disordered, Form A Fiber-like, some BR, no E |
| 77° C., SC to RT | 84 | XRPD OM | Amorphous/Form A mixture UM, melt-like no BE |
| 80° C., 1 day | 85 | XRPD OM | Form A[c] UM, opaque, no BE |
| 80° C., 3 hrs | 86 | XRPD OM | Form A[c] UM, melt-like + very small part. w/ BE |

[a]Starting material - sample no. 3. Temperature and duration of experiments are approximate
[b]Heating with agitation
[c]Minor peak shifts are attributable to the X-ray instrument used
BR; Birefringence;
E—Extinction Series of experiments targeting hydrate formation using both lot 5 and amorphous material generated during the screen as starting material are presented in Table 13 through Table 16. In particular, Table 13 and Table 15 present the results of various water activity slurry experiments. The conditions and results of antisolvent precipitation with water using lot 5 are summarized in Table 14. Table 16 presents the results of aqueous vapor stress experiments.

TABLE 13

Crystallization of compound 2 under Aqueous Conditions using Lot 5 (Form A) - Water Activity Slurries

| Conditions[a] | Water activity $(a_w)$[b] | Sample No. | Analytical Technique | Results |
|---|---|---|---|---|
| Acetone/water (80/20) RT, 5 days | 0.82 | 87 | XRPD OM | Form A UM, agglom., BE on smaller part. |
| Acetone/water (20/80) RT, 5 days | 0.96 | 88 | XRPD OM | Form A White, rhomboic plates, BE |
| Acetone/water (10/90) RT, 5 days | 0.97 | 89 | XRPD OM | Form A White, rhomboic plates, BE |
| ACN/water (67/33) 60° C., 3 days | 0.91 | 90 | XRPD OM | Form A UM, agglom., BE on smaller part. |
| Dioxane/water (50/50) 68° C., 9 days | 0.98 | 91 | XRPD OM | Form A Plate-like, BE |
| DMF/water (20/80) RT, 5 days. Washed w/ water | 0.93 | 92 | XRPD OM | Form A White, rhomboic plates, BE |
| DMF/water (10/90) RT, 5 days. Washed w/ water | 0.96 | 93 | XRPD OM | Form A White, rhomboic plates, BE |
| DMSO/water (20/80) RT, 5 days. Washed w/ water | 0.92 | 94 | XRPD OM | Form A White, rhomboic plates, BE |
| DMSO/water (10/90) RT, 5 days. Washed w/ water | 0.97 | 95 | XRPD OM | Form A White, rhomboic plates, BE |
| EtOH/water (20/80) RT, 5 days. Washed w/ EtOH | 0.95 | 96 | XRPD OM | Form A White, rhomboic plates, BE |

TABLE 13-continued

Crystallization of compound 2 under Aqueous Conditions using Lot 5 (Form A) - Water Activity Slurries

| Conditions[a] | Water activity ($a_w$)[b] | Sample No. | Analytical Technique | Results |
|---|---|---|---|---|
| EtOH/water (10/90) RT, 5 days. Washed w/ EtOH | 0.97 | 97 | XRPD OM | Form A White, rhomboic plates, BE |
| EtOH/water (10/90) 40° C., 4 days | 0.97 | 98 | XRPD OM | Form A White, rhomboic plates, BE |

[a]Percent-by-volume solvent ratio, temperature and duration of experiments are approximate
[b]Water activities were calculated using UNIFAC calculator (v. 3.0) at 25° C. The estimates were not performed under cGMP

TABLE 14

Crystallization of compound 2 under Aqueous Conditions using Lot 5 (Form A) - Solvent(S)/Antisolvent (AS) Precipitation

| Conditions[a] | Sample No. | Analytical Technique | Results |
|---|---|---|---|
| DMSO/water Diss. at 50° C., FC to RT, RT soln. into chilled AS (ppt) | 99 | XRPD OM | Form A[b] White, UM, no BE |
| THF/water Diss. at 50° C., FC to RT, RT soln. into chilled AS (ppt, sticky substance). Slurry, RT, 4 h | 100 | XRPD OM | Form A[b] Pale yellow, UM, no BE |
| DMF/water AS into soln. (ppt) | 101 | XRPD OM | Form A UM, agglom., opaque, no BE |
| DMF/water Diss. at 50° C., FC to RT, RT soln. into chilled AS (ppt) | 102 | XRPD OM | Form A[b] White, UM, no BE |
| Dioxane/water Hot soln. at 70° C. into RT AS (ppt). Centrifuged, decanted, dried w/ $N_2$ | 103 | XRPD OM | Form A UM, agglom., no BE + very small needles, BE |

[a]Temperature and duration of experiments are approximate
[b]Minor peak shifts are attributable to the X-ray instrument used

TABLE 15

Crystallization of compound 2 under Aqueous Conditions using Amorphous Material - Water Activity Slurries

| Conditions[a] | Water activity ($a_w$)[b] | Sample No. | Analytical Technique | Results |
|---|---|---|---|---|
| Acetone/water (88/12) | 0.73 | 104 | XRPD OM | Form A White, fine part., BE |
| Acetone/water (82/18) | 0.80 | 105 | XRPD OM | Form A White, fine part., BE |
| Acetone/water (60/40) | 0.89 | 106 | XRPD OM | Form A White, irregular plates, BE and UM, no BE |
| Acetone/water (33/67) Washed w/ acetone/water (33/67) | 0.93 | 107 | XRPD OM | Form A[c] White, UM, partial BE |
| Acetone/water (25/75) | 0.95 | 108 | XRPD OM | Form A[c] White, UM, no BE |
| Ethanol/water (80/20) | 0.70 | 109 | XRPD OM | Form A[c] White, irregular small plates, BE |
| Ethanol/water (70/30) | 0.80 | 110 | XRPD OM | Form A[c] White, plates and blades, BE and UM, no BE |
| EtOH/water (67/33) 40° C., 2 days | 0.82 | 111 | XRPD OM | Form A[c] White, tiny plates, BE and UM, no BE |
| Ethanol/water (47/53) | 0.90 | 112 | XRPD OM | Form A[c] White, UM, partial BE |
| Ethanol/water (20/80) | 0.95 | 113 | XRPD OM | Form A[c] White, fine part., BE |
| IPA/water (50/50) 40° C., 2 days | 0.96 | 114 | XRPD OM | Form A[c] White, tiny blades, BE and UM, no BE |
| DMF/water (9/91) RT, 5 days. Washed w/ water | 0.98 | 115 | XRPD OM | Form A[c] White, UM, no BE |

TABLE 15-continued

| | | | | |
|---|---|---|---|---|
| DMSO/water (10/90) RT, 5 days. Washed w/ water | 0.97 | 116 | XRPD OM | Form A[c] White, UM, no BE |
| MeOH/water (50/50) Washed w/ MeOH/water (50/50) | 0.75 | 117 | XRPD OM | Form A[c] White, fine part., BE and UM, no BE |
| THF/water (50/50) Washed w/ THF/water (50/50). VO, RT, 1 h. | 1.03 | 118 | XRPD OM | Form A[c] White, UM, no BE |

[a]Starting material - sample no. 3 unless otherwise indicated. Percent-by-volume solvent ratio, temperature and duration of experiments are approximate. The experiments were conducted at ambient conditions for 6 days unless otherwise indicated
[b]Water activities were calculated using UNIFAC calculator (v. 3.0) at 25° C. The estimates were not performed under cGMP
[c]Minor peak shifts are attributable to the X-ray instrument used

| Conditions[a] | Water activity $(a_w)^d$ | Sample No. | Analytical Technique | Results |
|---|---|---|---|---|
| Water, 50° C., 3 days[b] | 1 | 119 | XRPD OM | Material C (close to Form A + peaks) UM, agglom., no BE |
| | | 120 | TGA[e] | ~1.0 wt % loss between ~28° C. and ~192° C. Sharp weight loss at ~256° C. (onset) |
| Water, RT, 4 days[c] | 1 | 121 | XRPD OM | Form A UM, no BE |

[a]Starting material - sample no. 3 unless otherwise indicated. Percent-by-volume solvent ratio, temperature and duration of experiments are approximate. The experiments were conducted at ambient conditions for 6 days unless otherwise indicated
[b]Starting material - sample no. 2
[c]Surfactant was used as wetting agent
[d]Water activities were calculated using UNIFAC calculator (v. 3.0) at 25° C. The estimates were not performed under cGMP
[e]TGA was acquired on post X-ray material (sample no. 120)
VO—Vacuum oven

TABLE 16

Aqueous Vapor Stress of compound 2

| Starting Material[a] | Conditions[b] | Sample No. | Analytical Technique | Results |
|---|---|---|---|---|
| Form A | 85% RH, 2 days | 122 | XRPD OM | Form A UM, BE |
| | 75% RH, 40° C., 2 days | 123 | XRPD OM | Form A UM, BE |
| Amorphous | 75% RH, 40° C., 1 day | 124 | XRPD OM | Disordered, Form A UM, agglom., some BR, no E |
| | Sample no. 14 85% RH, 3 days | 125 | XRPD OM | No peaks UM, no BE |
| | 97% RH, RT, 6 days | 126 | XRPD OM | Amorphous/Form A mixture White, fine particles, partial BE |

[a]Starting material, Form A - compound 2 lot 5, amorphous - sample no. 3 unless otherwise indicated
[b]Relative humidity, temperature, and duration of experiments are approximate
[c]Non-cGMP sample due to insufficient documentation for RH jar
[d]From sample no. 127 - a subsample of sample no. 14

In the context of this specification, "disordered" crystalline means that the XRPD pattern for the material has broad peaks (relative to instrumental peak widths) and/or strong diffuse scattering (relative to the peaks). In an embodiment, disordered materials are:
  microcrystalline;
  crystalline with large defect density; or
  mixtures of crystalline and x-ray amorphous phases; or
or a combination of the above.
a. Material C Material C was produced under exclusive conditions by aqueous slurry of amorphous material at elevated temperature (~50° C.). The experimental conditions and TGA data for Material C suggested that the formation of hydrated material could be possible. However, any further experiments in aqueous media including slurries in organic solvent/water mixtures with various water activity as well as slurry in water using surfactant did not produce Material C, but resulted in Form A. The nature of Material C is, therefore, not known. The material could potentially be a crystalline degradant of compound 2 obtained by aqueous slurry at elevated temperature. Alternatively, Material C could be an unstable hydrate of compound 2 readily dehydrating at ambient. XRPD analysis of the amorphous material in a variable relative humidity chamber was not attempted but could potentially be of interest.
b. Material D Material D was produced in a single experiment by fast cooling of a methyl ethyl ketone/toluene (~4/1) solution to subambient temperature. The solids initially formed at subambient temperature were observed to dissolve upon equilibration at ambient conditions and reprecipitate when returned to subambient temperature. The exclusivity of solvent conditions suggested that the formation of solvated material could be possible. In particular, isolated cold and initially exhibiting birefringence with extinction indicative of crystallinity, the material displayed a disordered XRPD pattern when analyzed at room temperature (XRPD at subambient temperature was not attempted). This suggests partial loss of crystallinity potentially due to rapid loss of solvent upon storage under ambient conditions. The solvated nature of Material D was not confirmed as any further experiments targeting the material, including crystallization of amorphous material and submitted lot of compound 2 from various methyl ethyl ketone/toluene mixtures as well as the corresponding solvents individually did not produce Material D but resulted in Form A.

D. Preparation and Characterisation of Compound 2 Amorphous Material

Amorphous material initially generated during the polymorph screen was scaled up to provide an alternative starting material for screening. Scale-up experiments were performed at ~500 mg and ~1 g scale of the starting material using lot 5 of compound 2. The two samples were produced by lyophilization of a 1,4-dioxane solution, initially prepared at elevated temperature to facilitate dissolution and cooled to ambient.

Sample no. 2 was characterised by XRPD, TGA, DSC (standard and cycling), hotstage microscopy, moisture sorption analyses, and solution $^1$H NMR. Cycling DSC was acquired on sample no. 3 to verify whether the material was amorphous. Scale-up conditions are summarized in Table 17. Characterisation data are presented in Table 18.

TABLE 17

Scale Up of compound 2 Amorphous

| Conditions[a] | Sample ID | Analytical Technique | Results |
|---|---|---|---|
| 500 mg scale<br>Diss. in 1,4-dioxane at 70° C., SC to RT.<br>Lyophilization, −50° C. | 2 | XRPD<br>OM | Amorphous halo(s)<br>UM, opaque aggregates, no BE |
| 1 g scale<br>Diss. in 1,4-dioxane at 70° C.<br>SC to RT<br>Lyophilization, −50° C. | 3 | OM<br>DSC[b]<br>(cycling) | UM, opaque aggregates, no BE<br>Cycle 1: small step/endo event at ~57.2° C. (peak max).<br>Cycle 2: step change at ~50.6° C. (between ~46.6° C. and ~55.0° C.). Exo at ~123.7° C. followed by sharp endo at ~195.0° C. (peak max) |

[a]Starting material - compound 2 lot 5. Scale and temperature are approximate
[b]Cycle 1: heat from −50° C. to 70° C., cycle 2: cool from 70° C. back to −50° C. then heat to 250° C.

TABLE 18

Physical Characterisation of Scaled-Up compound 2 Amorphous

| Sample No. | Analytical Technique | Results |
|---|---|---|
| 2 | XRPD | Amorphous halo(s) |
|  | TGA | ~1.2 wt % loss between ~26° C. and ~71° C. Sharp weight loss at ~258° C. (onset) |
|  | DSC | Small step/endo event at ~54.3° C. (peak max), between ~34° C. and ~68° C. Exo at ~111.7° C. followed by sharp endo at ~190.7° C. (peak max) |
|  | DSC[a]<br>(cycling) | Cycle 1: small step/endo event at ~54.5° C. (peak max).<br>Cycle 2: step change at ~48.8° C. (between ~44.4° C. and ~53.2° C.). Exo at ~114.8° C. followed by sharp endo at ~194.5° C. (peak max) |
|  | HSM | 24.1° C. - Prior heating<br>31.2° C. - Heating, 10° C./min<br>41.4° C. - No change noted<br>48.9° C. - No change noted<br>60.2° C. - No change noted<br>70.1° C. - No change noted<br>79.6° C. - No change noted<br>90.5° C. -<br>105.4° C. - No change noted<br>116.2° C. - No change noted<br>160.5° C. - No change noted<br>183.5° C. - A few particles appear birefringent<br>186.0° C. - Solid-liquid began<br>186.6° C. - Solid-liquid complete, cooling<br>27.5° C. - No recrystallization noted |
|  | Moisture sorption | ~0.08 wt % gain upon equilibration at ~5% RH<br>~1.18 wt % gain between ~5% and ~75% RH<br>~8.69 wt % gain between ~75% and ~95% RH<br>~8.56 wt % loss between ~95% and ~5% RH. Large hysteresis between ~85% and ~15% RH upon desorption |

TABLE 18-continued

[a] Cycle 1: heat from −50° C. to 70° C., cycle 2: cool from 70° C. back to −50° C. then heat to 250° C.

| Sample No. | Analytical Technique | Results |
|---|---|---|
| 2 | $^1$H NMR | Consistent with chemical structure of compound 2 Likely contains residual dioxane based on peak at ~3.57 ppm. Small unidentified peaks at ~5.08 ppm, ~1.36 ppm, ~1.23 ppm and ~0.85 ppm[a] |
| 3 | DSC[b] (cycling) | Cycle 1: small step/endo event at ~57.2° C. (peak max). Cycle 2: step change at ~50.6° C. (between ~46.6° C. and ~55.0° C.). Exo at ~123.7° C. followed by sharp endo at ~195.0° C. (peak max) |

[a] Peaks at ~2.5 ppm and ~3.3 ppm are due to partially deuterated DMSO and water, respectively
[b] Cycle 1: heat from −50° C. to 70° C., cycle 2: cool from 70° C. back to −50° C. then heat to 250° C.

Overall the data for the two samples are consistent with amorphous material exhibiting a glass transition in the ~49-51° C. temperature range. Additional data acquired on sample no. 2 suggest that the material contains residual solvent and exhibits significant hygroscopicity, retaining significant amount moisture upon desorption over a broad range of relative humidity (~85-15% RH).

a. Sample No. 2

XRPD data for this sample are consistent with amorphous material exhibiting characteristic halos in its pattern and showing no evidence of sharp peaks.

Thermal data are consistent with the material containing residual solvent. The TGA curve showed a ~1.2 wt % loss between ~26° C. and ~71° C. that could be associated with the loss of retained moisture, based on hygroscopicity of the material. The release of residual dioxane may also contribute to the weight loss, as the presence of a small amount of dioxane was confirmed by NMR. Sharp weight loss was observed at ~258° C. (onset) likely due to decomposition of the material.

The DSC thermogram exhibited a small broad endothermic event at ~54.3° C. (peak maximum) in the ~34.0-68.0° C. range concurrent with the TGA loss. The event may be associated with desolvation of the material overlapped with the glass transition event, potentially with relaxation as suggested by temperature cycling DSC. A slightly broadened exotherm at ~111.7° C. (peak maximum) followed by a sharp endotherm at ~190.7° C. (peak maximum) were observed to be due to crystallization followed by melting based on hot-stage microscopy data. The results of heat stress experiments performed with amorphous material as well as DSC data acquired on Form A indicate that the material recrystallizes as Form A.

The temperature cycling DSC curve demonstrated a small broad endotherm at ~54.5° C. (peak maximum) during the first heating cycle attributable to desolvation based on TGA data. The glass transition temperature ($T_g$) of the material was observed at ~48.8° C. (mid point) as a step change of the base line during the second heating cycle. In addition, the thermogram exhibited a broadened exotherm at ~114.8° C. (peak maximum) followed by a sharp endotherm at ~194.5° C. (peak maximum) due to crystallization of Form A followed by its melting, as suggested previously.

Hotstage microscopy showed no visual changes below ~183.5° C. possibly due to small particle size expected for an amorphous substance. Some birefringence seen at ~183.5° C. is consistent with the crystallization of Form A based on DSC data and the results of heat stress experiments performed with the amorphous material. Solid liquid transition was observed between ~186.0° C. and ~186.6° C. due to melting of the recrystallized material.

Moisture sorption analysis data acquired on the sample are consistent with a material of significant hygroscopicity A ~0.1 wt % gain was observed upon equilibration at ~5% RH. The material gained approximately 1.2 wt % of water below ~75% RH and showed additional water uptake of ~8.7 wt % upon increasing the relative humidity to ~95%, with a total gain of ~9.9 wt %. Partial desorption occurred upon decreasing relative humidity to ~5% (~8.6 wt % loss between ~95% and ~5% RH) [5]. A large hysteresis was observed upon desorption between ~85% and ~15% RH indicating that the material retains a significant amount of moisture (~3.6-5.8 wt %) over a broad range of relative humidity. This behavior can be indicative of the existence of a hydrate. However, experiments targeting a hydrated form (Material C) were unsuccessful, possibly due to the existence of an unstable hydrate. Equilibrium was not reached between ~85% and ~95% RH and between ~15% and ~5% RH suggesting that even higher water uptakes would be possible.

The NMR chemical shifts and integral values for the material are consistent with the chemical structure of compound 2. The spectrum exhibited small additional peak at ~3.57 ppm attributable to residual dioxane. Small unidentified peaks at ~5.08 ppm, ~1.36 ppm, ~1.23 ppm and ~0.85 ppm were observed likely due to the presence of impurity.

b. Sample No. 3

Temperature cycling DSC data for this sample were similar to the data acquired for sample no. 2. The temperature cycling DSC curve exhibited a small broad endotherm at ~57.2° C. (peak maximum) during the first heating cycle possibly due to desolvation. The glass transition temperature ($T_g$) of the material was observed at ~50.6° C. (mid point) as a step change of the base line during the second heating cycle. In addition, the thermogram displayed broadened exotherm at ~123.7° C. (peak maximum) followed by a sharp endotherm at ~195.0° C. (peak maximum) due to crystallization of Form A followed by its melting as suggested previously.

E. Additional Characterisation of Compound 2 Form B (Ethyl Acetate Solvate)

In addition to physical characterisation of Form B (lot 3), partial characterisation of the samples of Form B generated during the screen was performed. Additional data were acquired on the material produced by organic vapor stress of amorphous material in ethyl acetate (sample no. 79) and the material obtained by crystallization of a solution of Form A in tetrahydrofuran/ethyl acetate following partial rotary evaporation (sample no. 48). The two materials were characterised by XRPD. Form B prepared from amorphous (sample no. 79) was also characterised by TGA and correlated thermogravimetric-infrared spectroscopy analysis (TG-IR). The data are presented in Table 19.

TABLE 19

Additional Physical Characterisation of compound 2
Form B (Ethyl Acetate Solvate)

| Sample | Analytical Technique | Results |
|---|---|---|
| Form B (sample no. 79) | XRPD | Crystalline consistent with Form B of compound 2 |
| | TGA | ~4.7 wt % loss between ~138° C. and ~190° C. Sharp weight loss at ~254° C. (onset) |
| | TG-IR | (TGA): ~4.8 wt % loss between ~144° C. and ~190° C. (IR): Consistent with loss of ethyl acetate. Background water due to insufficient helium purge |
| Form B (sample no. 48) | XRPD | Crystalline consistent with Form B of compound 2 |

Overall the data for the two materials are consistent with previously characterised Form B, a crystalline non-stoichiometric ethyl acetate solvate of compound 2.

XRPD data for the samples exhibited resolution of peaks indicative of crystalline material. The two materials displayed patterns consistent with the pattern of previously characterised lot 3 that was confirmed to contain ethyl acetate by NMR spectroscopy.

TGA data are consistent with a solvated material. The TGA curve for the material showed a ~4.7 wt % loss between ~138° C. and ~190° C. associated with the release of ethyl acetate based on TG-IR data. As previously suggested for lot 3, the high temperature of the release is consistent with the incorporation of the solvent within the crystal lattice. A sharp weight loss was observed at ~254° C. (onset) attributable to decomposition.

Correlated TG-IR data are consistent with a non-stoichiometric ethyl acetate solvate. Both TGA correlated data and Gram-Schmidt plot showed loss of volatile during heating. The Gram-Schmidt plot demonstrated an intensity maximum at ~9.1 minutes due to the volatile released. The TGA curve exhibited a weight loss of ~4.8% between ~144° C. and ~190° C. attributable to the loss of approximately 0.23 moles of ethyl acetate per mole of compound 2 as confirmed by the IR linked spectrum at ~9.1 minutes.

F. Partial Characterisation of Material C

Partial characterisation data were acquired on the material produced under exclusive conditions by aqueous slurry of amorphous material at ~50° C. (sample no. 119). The material was characterised by XRPD and TGA. The data are summarized in Table 15.

XRPD data for the material exhibited resolution of peaks indicative of crystalline material designated as Material C. Resembling the XRPD pattern of Form A, the pattern for Material C exhibited additional sharp peaks indicative of a possible mixture with new crystalline material. The TGA data showed a small weight loss of ~1.0 wt % loss between ~28° C. and ~192° C. Although the nature of the loss was not confirmed, it is likely associated with the release of water based on conditions of the material generation suggesting that some degree of hydration may be possible. A sharp weight loss was observed at ~256° C. (onset) attributable to decomposition.

The observed and prominent XRPD peaks for Material C are given in Tables 20 and 21 below.

TABLE 20

Observed peaks for Material C

| °2θ | d space (Å) | Intensity (%) |
|---|---|---|
| 8.0 ± 0.1 | 11.079 ± 0.140 | 21 |
| 8.3 ± 0.1 | 10.602 ± 0.128 | 22 |
| 9.8 ± 0.1 | 9.062 ± 0.094 | 26 |
| 10.3 ± 0.1 | 8.622 ± 0.085 | 28 |
| 10.9 ± 0.1 | 8.087 ± 0.074 | 14 |
| 11.8 ± 0.1 | 7.475 ± 0.063 | 40 |
| 13.1 ± 0.1 | 6.769 ± 0.052 | 38 |
| 14.1 ± 0.1 | 6.290 ± 0.045 | 26 |
| 14.7 ± 0.1 | 6.034 ± 0.041 | 25 |
| 15.7 ± 0.1 | 5.652 ± 0.036 | 51 |
| 16.1 ± 0.1 | 5.498 ± 0.034 | 66 |
| 16.7 ± 0.1 | 5.321 ± 0.032 | 84 |
| 17.6 ± 0.1 | 5.051 ± 0.029 | 40 |
| 17.9 ± 0.1 | 4.966 ± 0.028 | 100 |
| 18.5 ± 0.1 | 4.791 ± 0.026 | 43 |
| 19.3 ± 0.1 | 4.609 ± 0.024 | 55 |
| 19.6 ± 0.1 | 4.534 ± 0.023 | 28 |
| 20.6 ± 0.1 | 4.312 ± 0.021 | 48 |
| 21.5 ± 0.1 | 4.126 ± 0.019 | 43 |
| 22.4 ± 0.1 | 3.976 ± 0.018 | 78 |
| 23.5 ± 0.1 | 3.786 ± 0.016 | 57 |
| 23.9 ± 0.1 | 3.720 ± 0.015 | 96 |
| 24.0 ± 0.1 | 3.702 ± 0.015 | 95 |
| 24.5 ± 0.1 | 3.639 ± 0.015 | 69 |
| 25.0 ± 0.1 | 3.562 ± 0.014 | 59 |
| 25.7 ± 0.1 | 3.464 ± 0.013 | 40 |
| 26.2 ± 0.1 | 3.401 ± 0.013 | 29 |
| 26.7 ± 0.1 | 3.339 ± 0.012 | 57 |
| 27.3 ± 0.1 | 3.269 ± 0.012 | 50 |
| 28.7 ± 0.1 | 3.113 ± 0.011 | 29 |

TABLE 21

Prominent peaks for Material C

| °2θ | d space (Å) | Intensity (%) |
|---|---|---|
| 11.8 ± 0.1 | 7.475 ± 0.063 | 40 |
| 13.1 ± 0.1 | 6.769 ± 0.052 | 38 |
| 15.7 ± 0.1 | 5.652 ± 0.036 | 51 |
| 16.1 ± 0.1 | 5.498 ± 0.034 | 66 |
| 16.7 ± 0.1 | 5.296 ± 0.032 | 86 |
| 17.9 ± 0.1 | 4.966 ± 0.028 | 100 |
| 19.3 ± 0.1 | 4.609 ± 0.024 | 55 |

Material C was produced under exclusive conditions by aqueous slurry of amorphous material at elevated temperature (~50° C.). Resembling the XRPD pattern of Form A, the pattern for Material C exhibited additional sharp peaks indicative of a possible mixture with new crystalline material. A small weight loss (~1.0 wt %) observed upon heating, along with the conditions of the material generation suggested that Material C was the hydrate of compound 2. However, the nature of the loss was not confirmed as any further experiments in aqueous media targeting Material C, including slurries in organic solvent/water mixtures with various water activity as well as slurry in water using surfactant resulted in Form A.

Material D was produced under exclusive conditions, specifically by crystallization from a methyl ethyl ketone/toluene (~4/1) solution at subambient temperature. The exclusivity of the solvent system suggested that the formation of solvated material could be possible. Partial loss of crystallinity upon storage due to rapid loss of solvent was suggested for Material D based on XRPD data, but was not confirmed as any further experiments targeting the material, including crystallization from various methyl ethyl ketone/toluene mixtures as well as the corresponding solvents individually resulted in Form A.

The observed and prominent XRPD peaks for Material D are given in Tables 22 and 23 below.

TABLE 22

Observed peaks for Material D

| °2θ | d space (Å) | Intensity (%) |
|---|---|---|
| 8.9 ± 0.1 | 9.925 ± 0.112 | 69 |
| 10.0 ± 0.1 | 8.828 ± 0.089 | 56 |
| 12.7 ± 0.1 | 6.992 ± 0.055 | 23 |
| 15.5 ± 0.1 | 5.713 ± 0.037 | 62 |
| 16.1 ± 0.1 | 5.512 ± 0.034 | 94 |
| 19.7 ± 0.1 | 4.511 ± 0.023 | 75 |
| 21.4 ± 0.1 | 4.154 ± 0.019 | 100 |
| 24.2 ± 0.1 | 3.676 ± 0.015 | 85 |
| 25.3 ± 0.1 | 3.522 ± 0.014 | 55 |
| 25.8 ± 0.1 | 3.453 ± 0.013 | 53 |
| 27.4 ± 0.1 | 3.253 ± 0.012 | 46 |

TABLE 23

Prominent peaks for Material D

| °2θ | d space (Å) | Intensity (%) |
|---|---|---|
| 8.9 ± 0.1 | 9.925 ± 0.112 | 69 |
| 10.0 ± 0.1 | 8.828 ± 0.089 | 56 |
| 16.1 ± 0.1 | 5.512 ± 0.034 | 94 |
| 19.7 ± 0.1 | 4.511 ± 0.023 | 75 |
| 21.4 ± 0.1 | 4.154 ± 0.019 | 100 |

It will be appreciated that the invention may be modified within the scope of the appended claims.

What is claimed is:

1. Crystalline Form A of 1-[(3R)-6,8-difluoro-3,4-dihydro-2H-1-benzopyran-3-yl]-1,3-dihydro-5-[2-[(phenylmethyl)amino]ethyl]-2H-imidazole-2-thione, which is in unsolvated form, having an XRPD pattern with peaks at 14.0, 16.1, 16.6, 19.2 and 20.4°2θ±0.2°2θ.

2. Form A of 1-[(3R)-6,8-difluoro-3,4-dihydro-2H-1-benzopyran-3-yl]-1,3-dihydro-5-[2-[(phenylmethyl)amino]ethyl]-2H-imidazole-2-thione according to claim 1 having an XRPD pattern with further peaks at 15.6 and 18.4°2θ±0.2°2θ.

Figure 2:
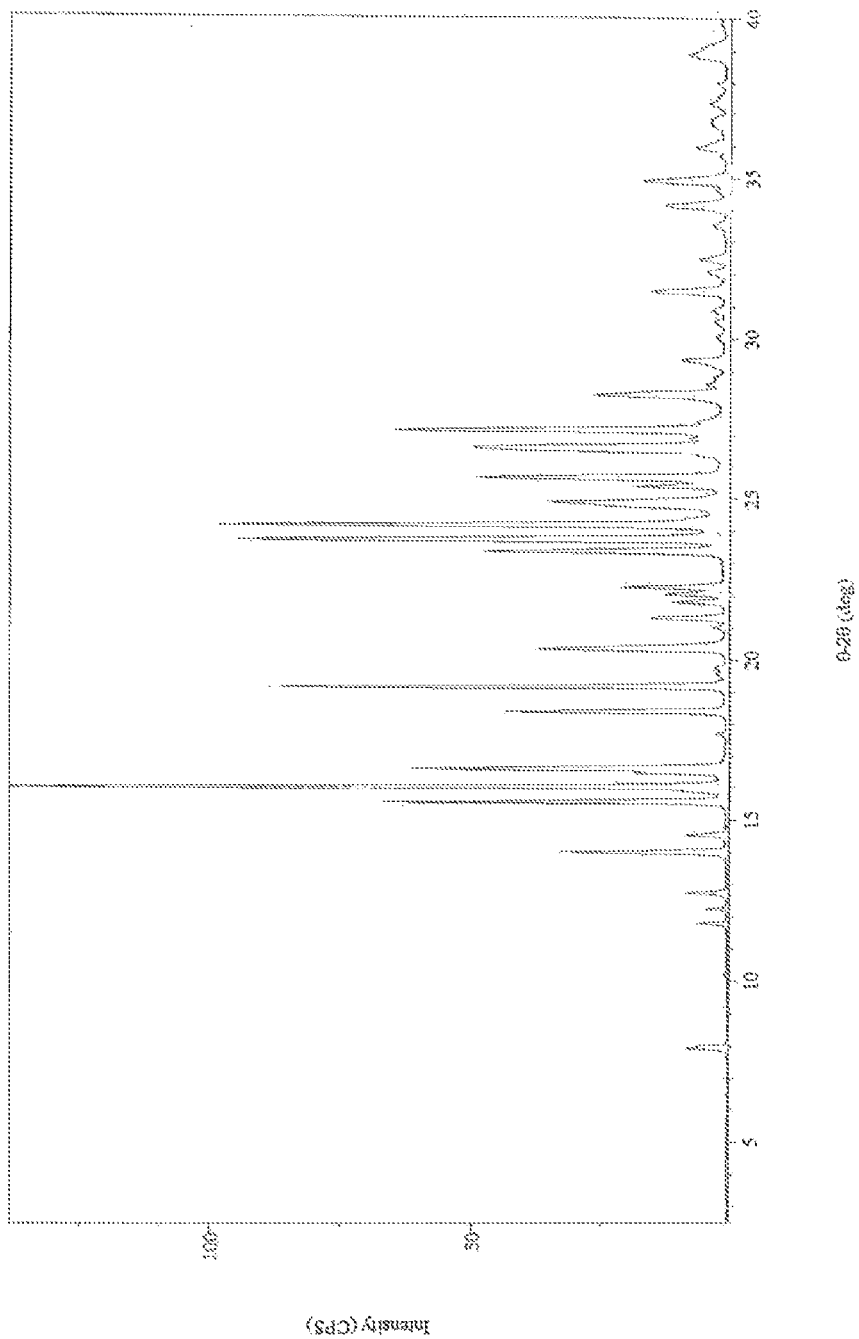
FIG. 2 shows the XRPD pattern of crystalline Form A of compound 2
PARAMETERS:
Panalytical X-Pert Pro MPD PW3040 Pro
X-ray tube: Cu(1.54059 Å)
Voltage: 45 kV
Amperage: 40 mA
Scan range: 1.01-40.00° 2θ
Step size: 0.017° 2θ
Collection time: 1940 s
Scan speed: 1.2°/min
Slit: Divergence slit (DS) before the mirror: ½°
Incident-beam antiscatter slit (SS): ¼°
Revolution time: 0.5 s
Mode: transmission
Image by File Monkey v3.2.3
Figure 3:
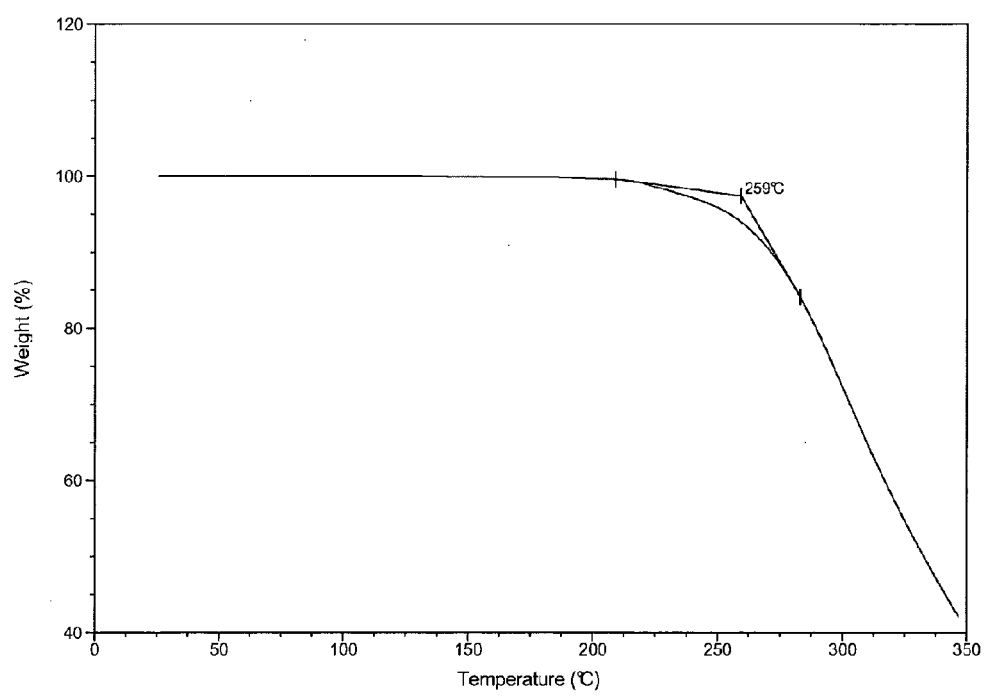
FIG. 3 shows the TGA thermogram of Form A of compound 2
Method: 00-350-10
Instrument: AutoTGA 2950 V5.4A
Universal V4.4A TA Instruments
Figure 4:
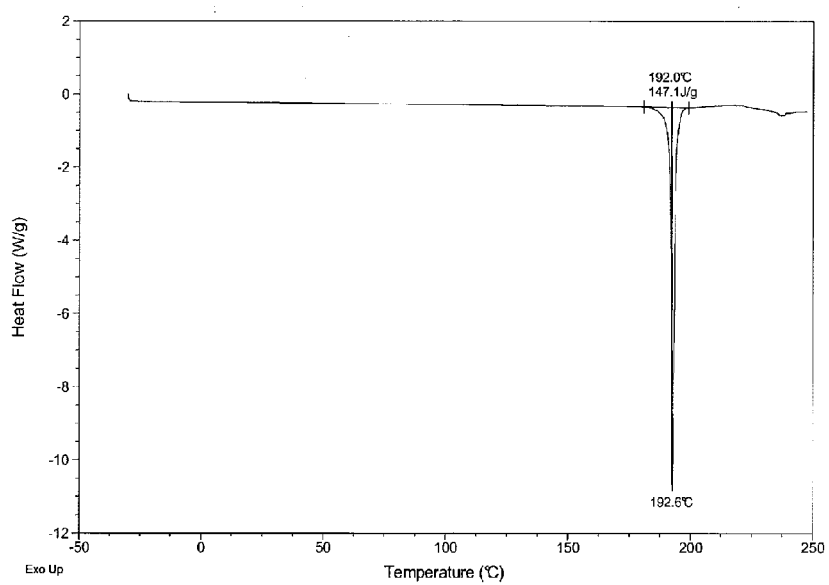
FIG. 4 shows the DSC thermogram of crystalline Form A of compound 2
Method: (−30)-250-10
Instrument: DSC Q2000 V23.10 Build 79
Universal V4.4A TA Instruments
Figure 5:
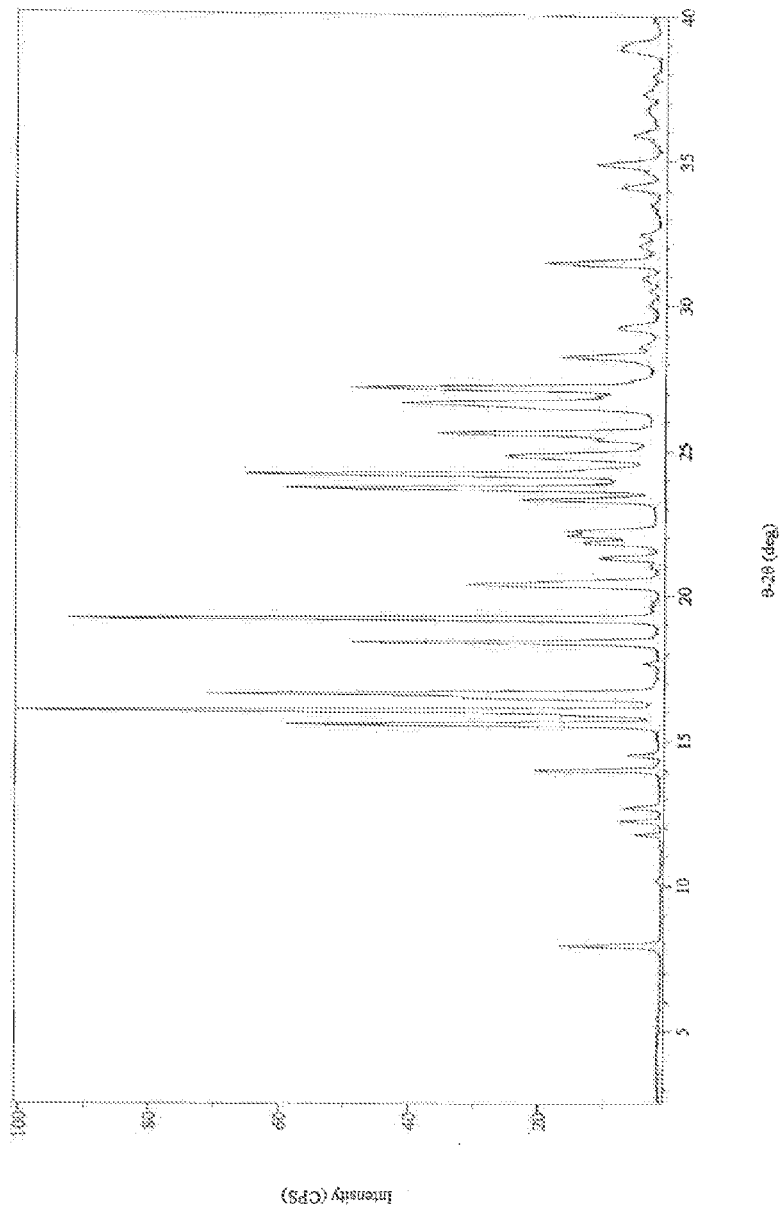
FIG. 5 shows the XRPD pattern of Form B of compound 2
PARAMETERS:
Panalytical X-Pert Pro MPD PW3040 Pro
X-ray tube: Cu(1.54059 Å)
Voltage: 45 kV
Amperage: 40 mA
Scan range: 1.01-39.99°2θ
Step size: 0.017°2θ
Collection time: 1939 s
Scan speed: 1.2°/min
Slit: Divergence slit (DS) before the mirror: ½°
Incident-beam antiscatter slit (SS): ¼°
Revolution time: 0.5 s
Mode: transmission
Image by File Monkey v3.2.3
Figure 6:
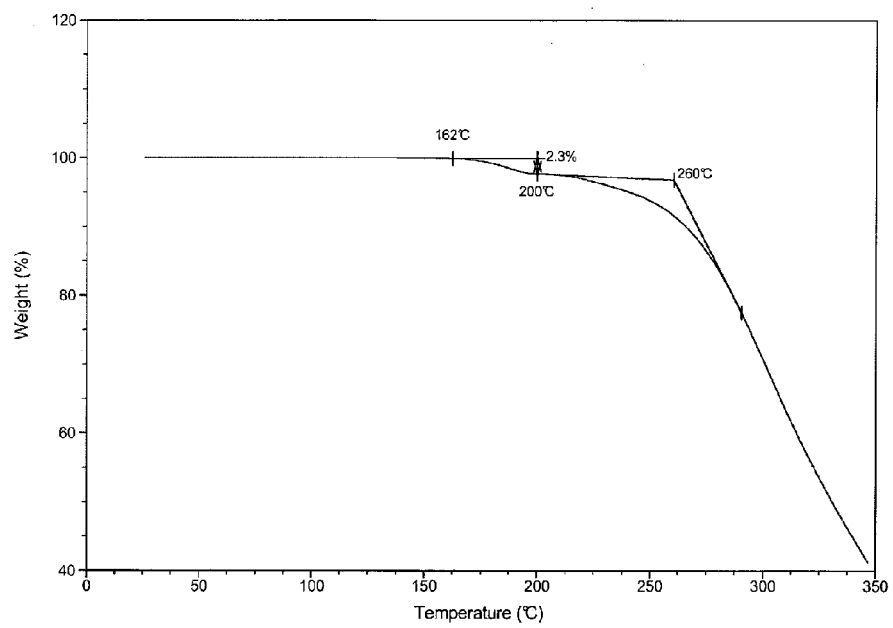
FIG. 6 shows a TGA thermogram of Form B of compound 2
Method: 00-350-10
Instrument: AutoTGA 2950 V5.4A
Universal V4.4A TA Instruments
Figure 7:
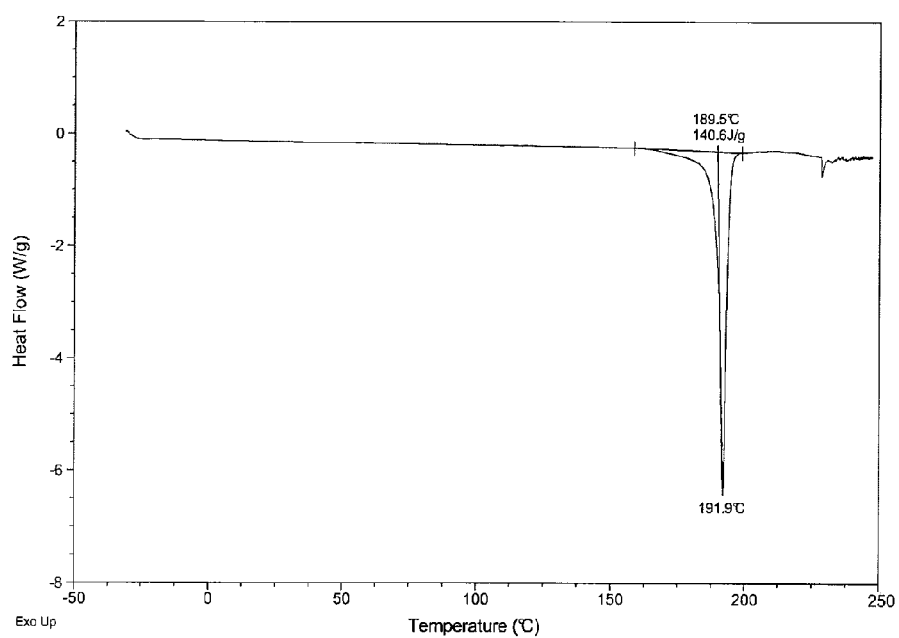
FIG. 7 shows the DSC thermogram of Form B of compound 2
Method: (−30)-250-10
Instrument: 2920 MDSC V2.6A
Universal V4.4A TA Instruments

3. Form A of 1-[(3R)-6,8-difluoro-3,4-dihydro-2H-1-benzopyran-3-yl]-1,3-dihydro-5-[2-[(phenylmethyl)amino]ethyl]-2H-imidazole-2-thione according to claim 1 having at least one of the following:

XRPD pattern as shown in FIG. 2;
a Thermogravimetric Analysis (TGA) thermogram showing a weight loss with an onset temperature of 259° C.±5° C.;
a TGA thermogram as shown in FIG. 3;
a Differential Scanning Calorimetry (DSC) thermogram showing an endothermic peak with an onset temperature of 192° C.±2° C. and a peak maximum at 193° C.±2° C.; and/or
a DSC thermogram as shown in FIG. 4.

4. A process to purify crystalline form A of (R)-5-(2-(benzylamino)ethyl)-1-(6,8-difluorochroman-3-yl)-1H-imidazole-2(3H)-thione as defined in claim 1 comprising the recrystallization of (R)-5-(2-(benzylamino)ethyl)-(6,8-difluorochroman-3-yl)-1H-imidazole-2(3H)-thione hydrochloride in at least one organic solvent.

5. A process according to claim 4 wherein the organic solvent is a mixture of toluene and methanol.

6. A process according to claim 5 wherein toluene and methanol are present in the mixture in a proportion of 62:38 w/w.

7. A process according to claim 5 wherein the organic solvent is distilled off and replaced with toluene.

8. A process according to claim 4 wherein the purification process further comprises the conversion of (R)-5-(2-(benzylamino)ethyl)-1-(6,8-difluorochroman-3-yl)-1H-imidazole-2(3H)-thione hydrochloride to (R)-5-(2-(benzylamino)ethyl)-1-(6,8-difluorochroman-3-yl)-1H-imidazole-2(3H)-thione.

9. A process according to claim 8 wherein the conversion of (R)-5-(2-(benzylamino)ethyl)-1-(6,8-difluorochroman-3-yl)-1H-imidazole-2(3H)-thione hydrochloride is achieved using an alkali metal hydroxide.

10. A process according to claim 9 wherein the alkali metal hydroxide is sodium hydroxide.

11. A process according to claim 8 wherein the conversion is carried out in a mixture of methanol and water.

12. A process according to claim 4, wherein the purity of (R)-5-(2-(benzylamino)ethyl)-1-(6,8-difluorochroman-3-yl)-1H-imidazole-2(3H)-thione is at least 95%, preferably at least 98%, most preferably ≥99.0%.

13. A process according to claim 4, wherein the purity of (R)-5-(2-(benzylamino)ethyl)-1-(6,8-difluorochroman-3-yl)-1H-imidazole-2(3H)-thione is at least 98%.

14. A process according to claim 4, wherein the purity of (R)-5-(2-(benzylamino)ethyl)-1-(6,8-difluorochroman-3-yl)-1H-imidazole-2(3H)-thione is ≥99.0%.

* * * * *